(12) United States Patent
Turkewitz et al.

(10) Patent No.: US 9,127,285 B2
(45) Date of Patent: Sep. 8, 2015

(54) GENETICALLY ALTERED CILIATES AND USES THEREOF

(71) Applicant: The University of Chicago, Chicago, IL (US)

(72) Inventors: Aaron Turkewitz, Chicago, IL (US); Joseph Briguglio, Chicago, IL (US)

(73) Assignee: The University of Chicago, Chicago, IL (US)

(*) Notice: Subject to any disclaimer, the term of this patent is extended or adjusted under 35 U.S.C. 154(b) by 0 days.

(21) Appl. No.: 13/773,327

(22) Filed: Feb. 21, 2013

(65) Prior Publication Data
US 2013/0224796 A1 Aug. 29, 2013

Related U.S. Application Data

(60) Provisional application No. 61/601,921, filed on Feb. 22, 2012.

(51) Int. Cl.
| | |
|---|---|
| C12P 21/06 | (2006.01) |
| C12N 15/79 | (2006.01) |
| C07K 14/44 | (2006.01) |
| C12P 21/04 | (2006.01) |
| C12P 21/02 | (2006.01) |
| C07H 21/02 | (2006.01) |
| C07K 14/00 | (2006.01) |
| C12N 15/00 | (2006.01) |

(52) U.S. Cl.
CPC .............. *C12N 15/79* (2013.01); *C07K 14/44* (2013.01); *C12P 21/02* (2013.01)

(58) Field of Classification Search
None
See application file for complete search history.

(56) References Cited

U.S. PATENT DOCUMENTS

| 6,087,124 A | 7/2000 | Steinbruck et al. ......... 435/69.1 |
| 6,846,481 B1 | 1/2005 | Gaertig et al. ............. 424/93.1 |
| 2006/0127973 A1 | 6/2006 | Hartmann et al. .......... 435/69.1 |

FOREIGN PATENT DOCUMENTS

| EP | 847 444 | 6/1998 |
| WO | WO 98/01572 | 1/1998 |
| WO | WO 03/078566 | 9/2003 |
| WO | WO 2007/006812 | 1/2007 |
| WO | WO 2010/108182 | 9/2010 |

OTHER PUBLICATIONS

Chilcoate et al., "An antisense approach to phenotype-based gene cloning in Tetrahymena" 98(15) Proceedings of the National Academy of Sciences 8709-8713 (2001).*
Yoon et al., "Enhanced Production and Secretion of Heterologous Proteins by the Filamentous Fungus *Aspergillus oryzae* via Disruption of Vacuolar Protein Sorting Receptor Gene Aovps10" 76(17) Applied and Environmental Microbiology 5718-5727 (2010).*
Eisen et al., "Macronuclear Genome Sequence of the Ciliate Tetrahymena thermophila, a Model Eurkaryote" 4(9) PLoS Biology1620-1642 (2006).*
Idiris et al. 85 Applied Microbiology and Biotechnology 667-677 "Enhanced protein secretion from multiprotease-deficient fission yeast by modification of its vacuolar protein sorting pathway" (2010).*
Turkewitz et al., "Functional genomics: the coming of age for *Tetrahymena thermophia*" 18(1) Trends in Genetics 35-40 (2002).*
Zeng et al., "The inactivation of the sortilin gene leads to a partial disruption of prosaposin trafficking to the lysosomes" 315 Experimenatl Cell Research 3112-3124 (2009).*
Becker and Rusing, *J. Eukaryot. Microbiol.*, 50:235-239, 2003.
Blomberg et al., *Mol. Cell Biol.*, 12 :7237-7747, 1997.
Boldrin et al., *Eukaryot Cell*, 2 :422-425, 2006.
Bruns et al., *Proc. Natl. Acad. Sci. USA*, 9 :284-286, 1985.
Brus and Cassidy-Hanley, *Meth. Cell Biol.*, 62:501-512, 2000.
Cassidy-Hanley et al., *Genetics*, 146:135-147, 1997.
Cowan et al., *Mol. Cell. Biol.*, 16 :4046-4060, 2005.
de Coninck et al., *J. Industr. Microbiol. Biotechnol.*, 24 :285, 2000.
Gaertig and Gorovsky, *Proc. Natl. Acad. Sci. USA*, 89:9196-9200, 1992.
Gaertig et al., Surface display of a parasite antigen in the ciliate Tetrahymena thermophila. *Nature Biotech.*, 17:462-465, 1999.
Gaertig et al., *Nucleic Acids Res.*, 22:5391-5398, 1994.
Hellenbroich et al., *Appl. Microbiol. Biotechnol.*, 51 :447, 1999.
Melia et al., Mutational analysis of regulated exocytosis in Tetrahymena. *J. Cell Sci.* 111(Pt1):131-140, 1998.
Orias et al., *Gene*, 2:295-301, 1988.
Shang et al., *Proc. Natl. Acad. Sci USA*, 6 :3734-379, 2002.
Spangler and Blackburn, *J. Biol. Chem.*, 10:6334-6340, 1985.
Taniguchi et al.,*j. Biol. Chem.*, 260 :13941-13946, 1985.
Tondravi and Yao, *Proc. Natl. Acad. Sci. USA*, 83:4369-4373, 1986.
Weide et al., *BMC Biotechnol.*, 6 :19, 2006.
Williams et al., *J. Biol. Chem*, 255:296-303, 1980.
Yu and Blackburn, *Proc. Natl. Acad. Sci. USA*, 21:8487-891, 1989.
Frankel, *Meth. Cell Biol.*, 62:27-125, 2000.
Gaertig and Kapler, Transient and stable DNA transformation of Tetrahymena thermophila by electroporation. *Meth. Cell Biol.*, 62:486-500, 2000.
Hai et al., Knockout heterokaryons enable facile mutagenic analysis of essential genes in Tetrahymena. *Meth. Cell Biol.*, 62:513-531, 2000.
Lin et al., The use of synthetic genes for the expression of ciliate proteins in heterologous systems. *Gene*, 288(1-2):85-94, 2002.
Pan et al., *Cell*, 28(3):595-604, 1982.
Turkewitz et al., "Regulated Protein Secretion in *Tetrahymena thermophila*." *Meth. Cell Biol.*, 62:347-362, 2000.

* cited by examiner

*Primary Examiner* — Anne Gussow
*Assistant Examiner* — Nancy J Leith
(74) *Attorney, Agent, or Firm* — Norton Rose Fulbright US LLP

(57) ABSTRACT

Ciliate organisms are provided that comprise reduced proteolytic processing in granules. For example, ciliates are provided that lack detectable expression of one or more sortilin (SOR) gene product. Methods for producing such genetically altered ciliates and methods for protein production in a these organisms are also provided.

20 Claims, 5 Drawing Sheets

| Fold-induction during regranulation | Fold-induction in exo- mutant (neg. control) | Statistical significance | Gene identity |
|---|---|---|---|
| 11.1 | 0.7 | 0.0008 | AP-3 adaptin large subunit |
| 30.0 | 1.2 | 0.001 | AP-3 medium subunit |
| 6.2 | 0.4 | 0.0003 | SEC14 |
| 11.2 | 1.1 | 0.0007 | Vps9 |
| 7.3 | 0.6 | 0.0006 | beta-arrestin-related |
| 16.1 | 0.7 | 0.0006 | GRIP domain protein |
| 7.2 | 0.4 | 0.004 | V-type ATPase |
| 7.8 | 1.0 | 0.0007 | vps10/sortilin (#1) |
| 7.5 | 1.2 | 0.0005 | Vps10/sortilin (#2) |
| 16.7 | 1.0 | 0.002 | tSNARE |
| 12.5 | 1.1 | 0.001 | synaptobrevin |
| 4.1 | 1.0 | 0.002 | Dynamin-related protein (DRP7) |
| 4.5 | 0.4 | 0.0006 | cathepsin |
| 5.8 | 0.7 | 0.0004 | carboxypeptidase |

SEQUENCE LISTING

<160> NUMBER OF SEQ ID NOS: 12

<210> SEQ ID NO 1
<211> LENGTH: 893
<212> TYPE: PRT
<213> ORGANISM: Tetrahymena thermophila

<400> SEQUENCE: 1

```
Met Lys Ala Tyr Lys His Leu Gln Leu Ile Gly Ile Val Leu Leu Ile
1               5                   10                  15

Ser Ala Leu Gln Phe Thr Ala Thr Ala Lys Gln Gln Asp Ile Ser Phe
            20                  25                  30

Ser Lys Asn Phe Leu Asp Ser Glu Ile Val Asp Val Ile Trp Cys Gly
        35                  40                  45

Thr Asp Thr Gln Asn Asp Gln Asn Val Leu Val Gln Thr Asp Ser Gly
    50                  55                  60

Thr Ile Tyr Arg Ser Gln Asn Lys Met Val His Phe Glu Asn Ile Ser
65                  70                  75                  80

Asp Asn Leu Val Asn Ala Gly Ile Lys Tyr Val Ala Asp Asn Ser Gln
                85                  90                  95

Ile Val Glu Ser Glu Val Ile Arg Met Ile Arg Ser Gln Ala Asn Pro
            100                 105                 110

Asn Val Ile Val Leu Gln Gly Lys Asn Glu Val Asn Trp Val Thr Arg
        115                 120                 125

Asp Cys Gly Asn Thr Phe Arg Ala Phe Ser Arg Lys Lys Asp Arg Ile
    130                 135                 140

Asn Thr Phe Lys Leu His Pro Ser Gln Glu Ala Trp Met Leu Ala Ser
145                 150                 155                 160

Thr Asn Asn Val Cys Ala Lys Ser Gln Lys Ala Pro Cys Phe Ser Phe
                165                 170                 175

Ala Ile Leu Trp Leu Ser Lys Asp Leu Gly Asn Ser Trp Glu Lys Leu
            180                 185                 190

Thr Gln Tyr Val Tyr Lys Phe Glu Trp Gly Asn Leu Asn Phe Thr Asn
        195                 200                 205

Ser Gln Val Pro Gln Gln Arg Ile Phe Trp Val Gln Glu Asp Gly Asn
    210                 215                 220

Lys Gln Asn Gln Asn Arg Tyr Gly Leu His Glu Lys Arg Asn Phe Tyr
225                 230                 235                 240

Tyr Ser Asp Asp Phe Leu Ala Ser Lys Lys Leu Leu Met Thr Lys Gly
                245                 250                 255

Asn Val Phe Tyr Ile Asp Tyr Asn Tyr Leu Tyr Val Val Gln Leu Leu
            260                 265                 270

Glu Gln Asn Ser Gln Gln Val Asn Leu Lys Val Ala Asn Pro Gln Asp
        275                 280                 285

Leu Asp Ile Lys Leu Arg Asp Val Gln Leu Gly Glu Lys Leu Gln Asn
    290                 295                 300

His Lys Phe Thr Ile Leu Asp Thr Arg Glu Gly Gln Val Phe Leu Asn
305                 310                 315                 320

Val Asn His Leu Gly Ser Thr Ser Pro Met Gly Thr Leu Tyr Ile Ser
                325                 330                 335

Asp Ser Leu Gly Ala Arg Phe Ser Ser Leu Gln Gly His Leu Arg
            340                 345                 350

Ser Glu Asn Gly Asp Thr Asp Phe Glu Arg Leu His Gly Ile Tyr Gly
        355                 360                 365
```

```
Ile Tyr Ile Ala Asn Val Tyr Glu Gln Lys Arg Arg Glu Glu Phe Glu
    370             375             380

Asn Met Tyr Ala Ser Glu Gln Asn Asp Asp Glu Asn Gln Gly Gln
385             390             395             400

Asp Ser Lys Asn Lys Lys Ser Asn Thr Ser Ile Lys Gln Asp Lys Lys
                405             410             415

Ala Val Lys Met Lys Asp Leu Val Thr Gln Lys Ile Gln Thr Met Ile
            420             425             430

Thr Phe Asp Lys Gly Gly Met Trp Ser Arg Ile Asn Ala Pro Thr Thr
        435             440             445

Asp Gln Glu Asn Lys Glu Ile Lys Cys Gly Asp Asn Cys Phe Leu Asn
450             455             460

Ile His Ser Asn Ser Asn Asp Leu Tyr Asn Ser Phe Tyr Ser Ser Lys
465             470             475             480

Asn Ala Val Gly Leu Val Leu Ala Asn Gly Asn Val Gly Lys Tyr Leu
                485             490             495

Ser His Ser Pro Thr Gln Val Asn Thr Tyr Leu Ser Arg Asp Ala Gly
            500             505             510

Leu Thr Trp Lys Gln Val Ile Gln Asn Gln Asp Leu Thr Ser Tyr Leu
        515             520             525

Phe Ile Leu Ser Met Ile Gln Lys Ile Lys Arg Gly Ala Tyr Val Phe
    530             535             540

Glu Ile Gly Asp His Gly Ser Ile Ile Val Met Ala Lys Asp Lys Asp
545             550             555             560

Tyr Gly Thr Thr Lys Phe Ile Glu Tyr Thr Leu Asp Glu Gly Ile Thr
                565             570             575

Trp Asn Gln Val Gln Ile Ser Asp Thr Asp Ile Glu Ile Asp Asn Ile
            580             585             590

Ile Thr Glu Pro Ser Asn Thr Gly Thr Ser Phe Met Val Leu Ala Lys
        595             600             605

Thr Leu Ser Thr Asp Lys Lys Gln Tyr Gly Leu Ala Ile Thr Ile Asp
    610             615             620

Phe Ala Asn Gln Phe Asn Arg Asn Cys Ser Gly Ala Thr Ser Pro Asp
625             630             635             640

Asp Pro Asp Ser Asp Tyr Glu Lys Trp Ile Pro His Ser Tyr Lys Ser
                645             650             655

Ser Gln Cys Leu Leu Gly Gln Lys Val Thr Tyr Ser Arg Lys Lys Gln
            660             665             670

Glu Ser Val Cys Leu Asn Gly Glu Asp Tyr Glu Arg Gln Ile Glu Leu
        675             680             685

Gln Ala Cys Val Cys Ser Glu Glu Asp Trp Glu Cys Asp Ile Gly Tyr
    690             695             700

Ile Arg Asn Gly Gln Asn Gly Pro Cys Val Lys Asp Gly Thr Leu Ser
705             710             715             720

Asp Glu Glu Tyr Glu Gly Val Ile Pro Glu Ile Cys Thr Asp Tyr Tyr
                725             730             735

Gln Val Ser Arg Gly Tyr Arg Lys Ile Pro Tyr Asn Thr Cys Gln Gly
            740             745             750

Gly Val Asn Tyr Ser Ala Glu Thr Arg Arg Cys Pro Gly Asn Ser Ile
        755             760             765

Phe Ser Phe Asn Thr Leu Lys Asn Leu Ile Leu Leu Ile Leu Ala Ile
    770             775             780

Ala Ala Ile Tyr Tyr Gly Ile Gln Tyr Lys Ser Gln Leu Ser Ser Leu
```

```
                785                 790                 795                 800
Leu Ile Tyr Leu Ser Ser Leu Ile Pro Leu Ile Tyr Ser His Arg Lys
                    805                 810                 815

Asp Tyr Ile Asp Phe Ser Lys Ala Lys Ser Asp His Glu Glu Lys Glu
                    820                 825                 830

Asn Lys Phe Met Asn Leu Phe Ser Phe Ser Asn Lys Lys Asn Val Asn
                    835                 840                 845

His Tyr Ser Asn Val Asn Glu Ser Glu Asp Tyr Glu Asp Ser Glu Asp
                    850                 855                 860

His Gln His Leu Asn Asn Gln Asn Tyr Asn His Leu Asn Gln His Asn
865                 870                 875                 880

Tyr Phe Thr Asp Asn Gln Asp Glu Glu Ser His Tyr Asp
                    885                 890

<210> SEQ ID NO 2
<211> LENGTH: 2784
<212> TYPE: DNA
<213> ORGANISM: Tetrahymena thermophila

<400> SEQUENCE: 2
aaaagtatta atatttagac ttaatgaaag cgtacaagca tttatagctc ataggtattg      60
tattgcttat ttcagctcta cagttcactg caacagctaa atagcaagat atttctttta    120
gcaagaactt tcttgattct gaaatagttg atgtcatttg gtgtggcacc gacacataga    180
atgactaaaa cgttttggtt caaactgata gtggaaccat ttatagatct taaaacaaaa    240
tggtacactt cgaaaatatt agcgataatc ttgttaatgc tggtatcaaa tatgtagctg    300
ataatagtta aatagtagaa agtgaagtta ttagaatgat aagaagtcaa gctaatccta    360
atgttattgt tctttaaggc aaaaatgaag tcaactgggt aacaagagac tgcgtaata    420 catttagagc cttttcaaga agaaagata gaataaacac atttaagttg catcccagtt     480
aagaagcatg gatgttagca agcactaata acgtttgtgc caaaagctaa aaagctccat    540
gcttttcttt tgctatacta tggttaagta agatttagg aaatagttgg gagaagctta     600
ctcaatatgt ttacaaattc gaatggggta atttaaactt tactaatagc taagttcctc    660
aacaaagaat attttgggtt taagaagatg gaaataagca aaaccaaaat agatatggat    720
tgcatgaaaa aagaaacttt tattacagcg atgacttttt agcttcaaag aagctactca    780
tgaccaaagg aaatgtcttt tacattgatt ataattacct ttatgttgtt caacttttag    840
aataaaattc atagcaagtt aacctaaaag ttgctaatcc ttaagactta gatattaaat    900
taagggatgt ttagttaggc gagaagctgt aaaaccataa gtttacaatt ttagatactc    960
gtgaaggata ggttttctta aatgtaaatc atttaggttc aacatctcct atgggtactc   1020
tttatatatc agactcatta ggtgctcgct tttcctcaag cttgtagggt catcttagaa   1080
gtgaaaatgg tgatacagat tttgagcgct tacatggaat ttatgaatt tatatagcaa    1140 atgtttatga ataaaaaga agagaagagt ttgagaatat gtatgcaagc gaataaaatg    1200
atgatgatga aaattaagga taagactcca aaaataaaaa aagcaataca tcaattaaat   1260
aggataaaaa agcagtaaag atgaaagatt tggtcaccca aaaaatatag acaatgatta   1320
ctttcgataa aggtggtatg tggagtagaa ttaatgctcc aaccacagac taggaaaaca   1380
aagaaattaa atgtggtgac aactgcttct taaatataca ttctaattct aatgacttat   1440
ataattcatt ctactcatca aaaaatgctg taggtttagt tttagcaaat ggaaatgttg   1500
gtaagtatct ttcacatagt ccaactcaag ttaatactta cctttcaaga gatgcaggtt   1560
```

-continued

```
taacttggaa ataagtaatt taaaattaag atttaacttc atatttattt attctttcaa   1620
tgatttaaaa gattaaaaga ggagcttatg ttttcgaaat aggtgatcat ggttcaataa   1680
tagttatggc taaagataag gattatggaa ccactaaatt tatcgaatat actttagatg   1740
aaggtattac ttggaaccaa gtttaaatat cagatactga tatcgaaata gataatataa   1800
taacagagcc atcaaatact ggaacctcat tcatggttct tgcaaaaaca ctatcaacag   1860
ataaaaaata atatggatta gctataacaa tagattttgc taatcagttt aatagaaact   1920
gttctggtgc aacaagtcca gatgatcctg attctgatta tgaaaatgg atacctcata   1980
gctataaatc atctcaatgt ctcttaggtt agaaagtgac ttactcacgt aaaaaacaag   2040
aatctgtttg cttaaatgga agattatg aaagacaaat agaactttaa gcatgtgtct   2100
gctctgaaga agactgggag tgtgatatcg gctatattag aaatggataa atggtccat    2160
gtgtaaagga tggaacactt agtgatgaag aatatgaagg agtgatccca gaaatatgta   2220
ctgattatta ttaagtaagt agaggttata gaaaaattcc ttacaataca tgctaaggag   2280
gtgtaaatta ttcagcggaa actagaagat gccctggaaa ttcaattttt agctttaata   2340
ctttaaaaaa tttgattctt ttgattttag ctattgcagc tatttattat ggaattcagt   2400
ataagagtta actctctagc ttgttaattt acttaagttc tttgatccct ctaatttatt   2460
ctcatcgtaa agattatatt gacttttcca aagcaaagtc agaccatgaa gaaaggaaa    2520
ataaatttat gaatctattt tcatttagca acaaaaaaaa tgttaatcat tacagcaacg   2580
taaatgaaag tgaagattat gaagatagtg aagatcatta acatcttaat aaccaaaatt   2640
acaatcattt aaattaacat aactattta ctgataacca agatgaagag agtcattatg    2700
attgaattta attaactaat tgatttttttg ttttttcata aatttctttg tagattaatt  2760
taatttaaaa ataattttaa tagt                                          2784
```

<210> SEQ ID NO 3
<211> LENGTH: 893
<212> TYPE: PRT
<213> ORGANISM: Tetrahymena thermophila

<400> SEQUENCE: 3

```
Met Lys Ile Lys Arg Asn Gln Gln Ile Ala Ile Ile Phe Ala Ile Phe
 1               5                  10                  15

Ile Leu Thr Ala Ile Gln Ala Ala Asp Asp Val Ala Asp Asp Lys Val
             20                  25                  30

Gln Gln Ala Ile Lys Ser Tyr Gln Lys Gln Val Asp Gly Gly Ile Leu
         35                  40                  45

Glu Phe Glu Trp Cys Gly Thr Asn Glu Ile Tyr Asn Asp Glu Thr Asp
     50                  55                  60

Arg Val Val Asp Gln Glu Val Glu Glu Ser Phe Asp Thr Arg Ile
 65                  70                  75                  80

Phe Val Leu Thr Asp Glu Gly Gln Val Phe Lys Ser Thr Asn Tyr Gly
                 85                  90                  95

Lys Ser Trp Val His Val Thr Lys Ser Phe Tyr Gly Ser Asn Asn Gln
            100                 105                 110

Pro Phe Phe Ser Thr Glu Val Ser Ile Ser Pro Val Asp Gly Lys Thr
        115                 120                 125

Val Tyr Ile Trp Gly His Lys Asp Thr Ser Tyr Val Ser Glu Glu Cys
    130                 135                 140

Gly Lys Thr Trp Lys Lys Leu Asn His Pro Ala Gly Leu Phe Asp Phe
```

-continued

```
            145                 150                 155                 160
        Arg Phe His Arg Lys Asn Lys Asn Trp Val Leu Ala Phe Thr Asn Ile
                            165                 170                 175
        Glu Cys Lys Arg Phe Asp Glu Asp Cys Glu Ser Asn Met Arg Asn Leu
                            180                 185                 190
        Tyr Val Ser Gln Asp Ala Gly Val Thr Phe Thr Phe Leu Ala Thr Lys
                            195                 200                 205
        Val Leu Glu Ala Ser Trp Asn Arg Met Asn Asn Phe Tyr Asn Val Asp
            210                 215                 220
        Ser Pro Gly Ile Leu Met Ala Val Gln Gln Glu Ser Gln Ser Asn Val
        225                 230                 235                 240
        Val Tyr Thr Glu Asp Phe Gly Lys Thr Met His Thr Val Gln Glu Gly
                            245                 250                 255
        Gly Asp Asn Phe Phe Gln Ala Glu Tyr Phe Leu Phe Leu Thr Val Lys
                            260                 265                 270
        Pro Lys Asn Ser Lys Arg Thr Tyr Asp Met Lys Ile Ala Thr Met Phe
                            275                 280                 285
        Asp Asp Phe Asn Tyr Tyr Val Glu Pro Lys Ser Leu Lys Leu Pro Phe
            290                 295                 300
        Glu Asn Thr Asp Gln Leu Ser Phe Thr Ile Leu Lys Ser Asp Gly Ala
        305                 310                 315                 320
        Met Val Phe Leu Ala Ile His His Glu Thr Gln Asn Met Trp Gln Ser
                            325                 330                 335
        Asn Ile Tyr Val Ser Asp Trp Arg Gly Tyr Asp Leu Thr Leu Ala Leu
                            340                 345                 350
        Leu Tyr Asn Val Arg Ala Pro Asn Gly Asp Cys Asp Phe Glu Lys Ile
                            355                 360                 365
        Glu Ser Asn Glu Gly Val Tyr Ile Ala Asn Thr Tyr Asp Val Glu Lys
            370                 375                 380
        Val Glu Lys Leu Arg Asn Glu Val Lys Lys Met Asp Ile Ser Thr Ala
        385                 390                 395                 400
        Lys Asn Lys Leu Gln Thr Lys Asp Lys Lys Asn Leu His Lys Glu Leu
                            405                 410                 415
        Thr Asn Tyr Arg Lys Ser Val Ile Ser Phe Asp Ser Gly Ser Ser Trp
                            420                 425                 430
        His Pro Ile Arg Ala Pro Ser Gln Arg Trp Asn Gly Lys Thr Val Val
                            435                 440                 445
        Cys Ser Gly Glu Cys Ser Leu His Leu Ala Gly Arg Thr Tyr Tyr Lys
                            450                 455                 460
        Lys Ser Gln Met Tyr Ser Ser Asn Ala Pro Gly Leu Ile Val Ala
        465                 470                 475                 480
        Leu Gly Ser Ile Gly Thr His Leu Glu Asn Asn Phe Asn Leu Leu Asn
                            485                 490                 495
        Thr Tyr Leu Ser Asn Asp Gly His Gln Trp Arg Glu Ile Leu Lys
                            500                 505                 510
        Gly Pro His Ile Phe Glu Ile Gly Asp His Gly Gly Ile Ile Val Ala
                            515                 520                 525
        Ala Ser Val Ala Asn Lys Thr Asn Ile Ile Lys Tyr Ser Trp Asp Glu
        530                 535                 540
        Gly Lys Thr Trp Ser Glu Tyr Lys Leu Ser Ala Leu Pro Phe Glu Ile
        545                 550                 555                 560
        Asp Gln Ile Ile Thr Glu Pro Ser Asn Met Glu Gln Arg Phe Val Val
                            565                 570                 575
```

```
Tyr Gly Lys Gly Arg Asn Gly Thr Glu Thr Ser Met Ile Val Ser Val
            580                 585                 590

Asp Leu Gln Asp Leu His Ile Arg Gly Cys Val Gly Ala Glu His Pro
        595                 600                 605

Asn Arg Pro Asn Ser Asp Tyr Glu Ile Trp Ile Pro Thr Asn Phe Lys
610                 615                 620

Gly Glu Gln Cys Ile Phe Gly Arg Lys Val Lys Tyr Val Arg Arg Lys
625                 630                 635                 640

Pro Asp Ala Lys Cys Phe Asn Ser Ile Thr Thr Asp Gln Lys Thr Val
                645                 650                 655

Ile Glu Glu Cys Pro Cys Thr Gln Glu Asp Trp Glu Cys Asp Phe Gly
            660                 665                 670

Phe Tyr Arg Lys Glu Asn Glu Leu Glu Cys Ile Pro Met Asn Glu His
        675                 680                 685

Tyr Ser Pro Asp Asn Leu Ala Lys Pro Pro Ala Asp Cys Ser Trp Ser
690                 695                 700

Tyr Leu Val Ser Lys Gly Tyr Arg Lys Ile Pro Gly Val Phe Cys Gln
705                 710                 715                 720

Gly Gly Val Asp Leu Ser Pro Glu Tyr Lys Glu Cys Pro Pro Lys Ile
                725                 730                 735

Ser Val Pro Arg Thr Glu Glu Glu Thr Asp Gln Tyr Lys Ser Phe Lys
            740                 745                 750

Glu Ala Gln Lys Glu Ile Ile Ser Gln Tyr Gln Gln Gln Gln Gln Gln
        755                 760                 765

Ser Asn Ser Gln Asn Gly Lys Thr Asp Ser Ser Ser Ile Asn Trp
770                 775                 780

Gly Val Ile Phe Thr Gln Ile Phe Tyr Ala Gly Leu Ile Leu Thr Ala
785                 790                 795                 800

Leu Ala Leu Ala Phe Ile Phe Arg Glu Asn Ile Lys Gln Val Val Lys
                805                 810                 815

Ser Ile Gly Glu Ile Gly His Asn Lys Glu Arg Lys Gln Tyr Gln Gln
            820                 825                 830

Leu Gln Ser Ser Gln Asn Lys Gln Ser Ser Tyr Thr Gln Gln Lys Asn
        835                 840                 845

Thr Gln Asn Val Arg Ile Gln Glu Thr Glu Glu Arg Asn Tyr Asp Leu
850                 855                 860

Glu Glu Gln Asp Met His Tyr Pro Glu Asp Glu Lys Pro Val Leu Gln
865                 870                 875                 880

Arg Asp Gln Glu Asp Tyr Tyr Tyr Gln Glu Asp Tyr Asp
                885                 890
```

<210> SEQ ID NO 4
<211> LENGTH: 2682
<212> TYPE: DNA
<213> ORGANISM: Tetrahymena thermophila

<400> SEQUENCE: 4

```
atgaaaataa aaaggaatta gcaaattgca attatatttg ctattttcat cttgactgct    60
atttaggcag cagatgatgt tgcagatgat aaggtttagt aagctataaa agtattataa   120
aagtaagtag atggaggtat tttagaattc gagtggtgtg gtacaaatga aatttataac   180
gatgaaactg accgtgttgt tgttgattaa gaagttgaag aatcattcga tactcgtata   240
tttgttctta cagatgaagg ttaagttttt aaaagtacaa actatggtaa aagttgggtc   300
```

```
catgtcacta aatccttta tggttcaaat aattagccat ttttctctac tgaagtttcc    360
atttctcctg ttgatggtaa aacagtctat atttggggac acaaggatac cagctatgtt    420
tctgaggaat gtggtaagac ttggaaaaag ttaaaccatc ctgctggttt gtttgatttt    480
agatttcacc gtaaaaataa aaattgggta ttagctttca ctaatataga atgtaagaga    540
tttgatgaag attgtgaatc taatatgaga aatctttacg tttcttaaga tgcgggtgtt    600
actttcacat tcttagctac taaagtttta gaagcttcat ggaatagaat gaataacttt    660
tacaacgttg acagtcctgg tattttaatg gccgttcaat aagaatcata agtaatgta    720
gtttacactg aagacttcgg taaaactatg cacacagttt aagaaggtgg tgataatttc    780
ttttaagcag agtacttcct ctttttaaca gttaagccta aaaacagtaa aagaacctat    840
gatatgaaaa tcgcaactat gtttgacgat tttaattact atgttgaacc caaaagctta    900
aagcttccct ttgaaaacac tgattaactt tcgtttacaa ttctaaagag cgatggtgcc    960
atggttttcc ttgccataca ccacgaaact caaaatatgt ggtaaagcaa tatctatgtt   1020
tctgattgga gaggttatga tttgacttta gctttacttt acaatgttag agctccaaac   1080
ggagattgcg actttgaaaa gatagaaagc aatgaaggtg tttatatagc aaatacatat   1140
gatgttgaaa agttgaaaa attaagaaac gaagttaaaa aaatggatat cagcactgca   1200
aagaataaat tataaacaaa agataaaaag aatttgcaca agaactaac taattatagg   1260
aaatcagtca tttcatttga cagcggttct agttggcatc caattagagc tccttcatag   1320
agatggaatg gaaagactgt tgtttgcagt ggagaatgca gtttgcattt agctggtaga   1380
acatattata aaaaatctta gatgtattct tcctctaacg ctcctggttt aattgttgca   1440
ttaggaagca ttggaactca tcttgaaaac aacttcaatc ttcttaacac atatctttca   1500
aacgatggtg gtcactaatg gcgtgaaatt cttaagggtc ctcatatttt tgaaattggt   1560
gatcatggtg gtatcatcgt agctgcttct gttgccaata aaacaaatat catcaaatac   1620
agttgggatg aaggaaaaac atggagcgaa atataaattga gtgctttacc atttgaaata   1680
gattaaataa ttactgagcc tagcaatatg gaacagagat ttgttgttta tggaaaagga   1740
agaaatggaa cagaaacttc tatgattgtt tctgtagatt tataagattt gcacattaga   1800
ggttgtgtag gagctgaaca tcctaataga cctaatagtg attatgaaat ctggattcct   1860
actaattta aaggtgaaca atgtattttc ggtcgtaaag ttaaatatgt tagaagaaag   1920
cctgatgcaa aatgctttaa ttctatcaca acagattaaa aaacagttat tgaagaatgc   1980
ccatgcacat aagaagattg ggaatgtgac ttcggtttct acagaaaaga aaacgaatta   2040
gaatgtattc caatgaatga gcattattct cctgataatc ttgctaaacc tcctgcagat   2100
tgtagttggt cttacttagt ctcaaaggga tatagaaaaa taccaggagt atttttgttaa   2160
ggaggtgttg atttaagtcc agaatataaa gaatgtcctc caaaaatatc agtgcctaga   2220
actgaagaag aaacagatta atataaaagc ttcaaagaag cataaaaaga gattattagc   2280
taatattaat agtaatagta gtaatcaaat agttaaaatg gaaaaactga ttcatcatct   2340
tcaataaact ggggtgttat tttacataa attttctatg ctggattaat tttaacagct   2400
ttagctttag ctttcatatt tagagagaat atcaaataag tagtaaaaag cattggtgaa   2460
ataggacata ataaagaacg caaataatat taataactct aatcatctta gaataaataa   2520
tcatcataca cttaatagaa aaatactcaa aatgtccgca tttaagaaac tgaagaaaga   2580
aattatgatt tagaagaata agacatgcat tatccagaag atgaaaagcc tgtcttgtaa   2640
agagatcaag aagattacta ttattaagaa gattacgatt ga                     2682
```

<210> SEQ ID NO 5
<211> LENGTH: 936
<212> TYPE: PRT
<213> ORGANISM: Tetrahymena thermophila

<400> SEQUENCE: 5

```
Met Lys Lys Glu Ile Arg Ile Ala Leu Ile Ala Leu Phe Cys Cys Ile
1               5                   10                  15

Leu Thr Val Asn Cys Arg Asn Glu Tyr Ser Ser Val Ile Gly Asn
            20                  25                  30

Pro Ser Ser Leu Asp Ser Pro Leu Gln Asp Ile Gln Trp Cys Gly Glu
        35                  40                  45

Asn Ser Ser Asn Asp Asn Leu Val Val Leu Thr Gln Lys Gly Ser
    50                  55                  60

Val Tyr Arg Ser Glu Asp Arg Gly Ala Ser Trp Ile Lys Met Val Asp
65                  70                  75                  80

Ser Phe Ala Arg Val Gly Val Asn Val Lys Met Asp Leu Ser Ser Asn
                85                  90                  95

Val Gly Ile Val Thr Gln Met Ile Ala Ser Pro Ile Asp Ser Asn Glu
            100                 105                 110

Ile Val Phe Met Gly Ser Asp Gly Ile Asn Trp Ile Thr Thr Asp Cys
        115                 120                 125

Gly Val Thr Ile Gln Ala Leu Gly Ile Asn Leu Asn Leu Arg Glu Phe
    130                 135                 140

Met Tyr His Pro Thr Glu Lys Asn Trp Met Leu Ala Ser Ser Phe Asn
145                 150                 155                 160

Asn Cys Glu Lys Gln Asn Asn Gln Lys Asp Lys Arg Lys Lys Asp Thr
                165                 170                 175

Glu Cys Phe Lys Thr Lys Asp Leu Phe Phe Ser Glu Asn Lys Gly Lys
            180                 185                 190

Ser Trp Arg Val Leu Leu Lys Tyr Val Val Gln Phe Gly Trp Ala His
        195                 200                 205

Lys Val Asn Ser Lys Leu Thr Asn Val Pro Thr Ser Arg Ile Ile Tyr
    210                 215                 220

Ser Lys Glu Val Gly Ser Asn Ser Phe Phe Asn Glu Ala Ser Gln
225                 230                 235                 240

Gln Thr Asn Ile Ile Lys Asp Ser Gly His Gln Val Met Lys Gly
                245                 250                 255

Trp Ser Met Lys Thr His Leu Phe Tyr Thr Asp Asp Phe Met Lys Asn
            260                 265                 270

Gln Asn Met Ile Val Asn Gln Gly Asn Lys Phe Leu Ile Thr Glu Asn
        275                 280                 285

Tyr Leu Phe Ala Ala Gln Val His Ser Ser Asp Asn Gln Leu Val Lys
    290                 295                 300

Leu Met Val Ser Gln Ser Asn Gln Lys Glu Tyr Ser Phe Thr Tyr Ala
305                 310                 315                 320

Glu Ile Pro Glu Asp Ile His Gln His Ser Phe Thr Ile Leu Asp Thr
                325                 330                 335

Lys Glu Gly Gln Val Phe Leu Asn Ile Asn His Leu Gly Ser Asn Ser
            340                 345                 350

Pro Met Gly Asn Ile Tyr Gln Ser Asp Ser Thr Gly Thr Arg Phe Ser
        355                 360                 365

Leu Ser Leu Glu Asp Asn Val Arg Gly Arg Asp Gly Gln Cys Asp Phe
```

```
                    370                 375                 380
Glu Ser Val Asn Gly Val Glu Gly Ile Phe Ile Ser Asn Ile Phe Ala
385                 390                 395                 400

Pro Ser Lys Lys Leu Lys Gly Ile Lys Gln Met Leu Lys Ser Lys Asn
                    405                 410                 415

Pro Asp Thr Ser Asp Glu Asp Ile Pro Thr Glu Asn Thr Arg Lys Lys
                    420                 425                 430

Gly Gln Ala Gln Asn Ser Glu Asp Val Leu Lys Glu Ser Leu Lys Ser
                    435                 440                 445

Leu Arg Asp Asn Met Val Thr Arg Ile Thr Phe Asp Lys Gly Gly Met
                    450                 455                 460

Trp Ser Leu Leu Arg Ala Pro Ala Lys Asp Ser Asn Gly Lys Gln Ile
465                 470                 475                 480

Asn Cys Asp Ile Asn Lys Lys Cys Ser Leu His Leu His Ser Val Ser
                    485                 490                 495

Ser Gln Leu Ser Phe Gly Pro Ala Tyr Ser Ser Glu Asn Ser Leu Gly
                    500                 505                 510

Leu Ile Ile Ala Thr Gly Asn Thr Gly Gln Phe Leu Ser His Lys Ala
                    515                 520                 525

Gly Ser Val Asn Thr Tyr Leu Ser Arg Asp Gly Gly Leu Val Trp Glu
                    530                 535                 540

Glu Ile Arg Lys Gly Ser His Ile Tyr Glu Val Ala Asp His Gly Ser
545                 550                 555                 560

Ile Ile Val Met Ala Thr Asp Gln Glu Pro Thr Lys Asn Ile Ile Phe
                    565                 570                 575

Ser Trp Asp Glu Gly Arg Thr Trp Asn Thr Lys Gln Ile Ser Asp Thr
                    580                 585                 590

Pro Val Met Ile Ser Asn Ile Ile Thr Glu Pro Gly Asn Thr Ser Asp
                    595                 600                 605

Lys Phe Leu Val Tyr Gly Ser Ile Glu Gly Glu Ser Asp Ile Ser Gly
                    610                 615                 620

Ile Ile Val Leu Leu Asp Phe Ala Ser Leu His Pro Arg Asp Cys Gln
625                 630                 635                 640

Gly Tyr Glu Asn Pro Asp Thr Ser Asp Ser Asp Tyr Glu Tyr Trp Thr
                    645                 650                 655

Pro His Asn Pro Ser Glu Phe Cys Leu Leu Gly Arg Glu Ile Lys Tyr
                    660                 665                 670

Val Arg Arg Lys Arg Asp Ala Ala Cys Phe Asn Pro Glu Thr Phe Glu
                    675                 680                 685

Arg Ser Tyr Val Val Arg Lys Cys Glu Cys Thr Glu Leu Asp Trp Glu
                    690                 695                 700

Cys Asp Val Gly Phe Ala Arg Ala Lys Asp Asp Ser Lys Glu Arg Thr
705                 710                 715                 720

Gly Pro Cys Val Pro Leu Lys Asp Phe Lys Val Asp Tyr Asn Pro Pro
                    725                 730                 735

Gln Thr Cys Ser Gly Ser Tyr Gln Val Thr Gln Gly Tyr Arg Arg Val
                    740                 745                 750

Ala Gly Asn Gln Cys Ile Gly Gly Ile Asp His Ala Pro Ile Gln Tyr
                    755                 760                 765

Pro Cys Pro Met Phe Gly Phe Leu Ser Tyr Asn Asn Leu Phe Thr Asn
                    770                 775                 780

Val Leu Ile Leu Gly Ala Met Ala Gly Val Phe Tyr Leu Ile Ile Gln
785                 790                 795                 800
```

```
Asn Lys Glu Val Val Ile Thr Phe Val Ala Thr Ser Asn Leu Asp Ala
            805                 810                 815
Tyr Ile Asn Leu Gly Lys Thr Tyr Leu Lys Lys Gly Tyr Thr Phe Val
        820                 825                 830
Thr Ser Ile Val Leu Pro Gln Ala Ser Asn Gln Gln Gln Gly Tyr Phe
            835                 840                 845
Gln Ala Asn Gln Asp Glu Glu Asn Arg Lys Ser His Ser Leu Lys Asp
    850                 855                 860
Gln His His Gln Phe His Asp Asn Leu Ile Glu Ser His Asp His Asp
865                 870                 875                 880
Asp Glu Glu Glu Gln Ser Asp Ala Val Gln Gln Leu Thr Ser Ser
                885                 890                 895
Gln Val Pro Gln Asn Asn Ser Asn Lys Asn Asn Asn Ser Asn Thr
            900                 905                 910
Pro Asn Gln Ala Gln His Lys Asp Leu Leu Asp Glu His Asp Gly Glu
        915                 920                 925
Glu Asp Pro Phe Asp Pro Arg Asn
    930                 935

<210> SEQ ID NO 6
<211> LENGTH: 3010
<212> TYPE: DNA
<213> ORGANISM: Tetrahymena thermophila

<400> SEQUENCE: 6
atgaaaaaag aaataagaat agctcttata gctttatttt gctgcatttt gacagtaaat      60
tgtagaaatg aatactcaag cagtgtcatt ggaaccccct caagtttgga ttcacctctt     120
taggacattt aatggtgtgg tgaaaattca tcaaatgata atttggttgt cctcttaact     180
taaaagggta gcgtttacag atcagaagat agaggagcat cttggataaa gatggttgac     240
tcttttgcga gagttggtgt aaatgtaaag atggatctga gctcaaacgt aggtattgtt     300
acttaaatga ttgcaagtcc tattgattct aatgaaatag tctttatggg ctctgatggt     360
attaactgga tcactactga ttgtggtgtt accatttaag cccttggaat caacttaaat     420
ttgagagaat ttatgtatca cccaactgaa agaattgga tgcttgcttc ttcctttaac      480
aactgtgaaa agcaaacaa ccaaaaagat aagagaaaaa aggacactga atgctttaag     540
actaaagatt tgtttttctc tgaaaataag ggtaaaagct ggagagtttt acttaaatat     600
gttgtacaat tcggatgggc tcacaaagtt aattctaagc taacaaatgt cccaacttca     660
agaattatat actctaagga agtcggaagt aattcgtttt tctttaatga agcatctcaa     720
taaactaata taataataaa agatagtggt caccaagtga tgaagggttg agcatgaaa     780 actcatttat tctatactga tgatttcatg aaaaactaga atatgattgt taactaagga     840
aataagtttt tgattactga aaactacttg ttcgctgcat aagttcacag tagtgataat     900
taactagtca agttaatggt ttcttaatct aattaaaaag aatactcttt cacttatgct     960
gaaattcctg aagatataca ctagcactca ttcactattt tagatactaa ggaaggttag    1020
gtattcttaa atattaatca cttgggcagt aactctccta tgggtaatat ttactaatct    1080
gactcaactg gtactcgttt ctctctttct cttgaagata atgtaagagg aagagatggt    1140
taatgcgatt ttgaatcagt taatggtgtt gaaggtattt ttatctcaaa tatattcgct    1200
cctagcaaaa agttaagggg tatcaagcaa atgttgaaat ccaaaaatcc tgatacaagc    1260
gatgaagata ttccaactga aaacacaaga agaaaggtc aagcataaaa ttctgaagat     1320
```

```
gtcttaaaag aatccttaaa aagtcttaga gataacatgg taactcgtat cactttcgac    1380
aagggtggta tgtggagttt gcttagggct cctgctaaag attctaatgg aaaataaatt    1440
aattgtgata ttaataaaaa gtgttctctt caccttcact cagtttcttc ataactaagt    1500
tttggacctg cttactcaag tgaaaattca ttaggtttaa ttattgctac tggtaacaca    1560
ggataattct taagtcataa agcaggtagc gtcaacactt atctttctcg tgatggtggt    1620
cttgtttggg aagaaatccg taggggtct cacatatatg aagttgctga tcatggctct    1680
atcatagtta tggctactga ttaagaacct actaagaaca ttattttctc ttgggatgaa    1740
ggccgcacat ggaacaccaa gtaaattagc gatactcctg tcatgatttc aaatattatc    1800
actgaacctg gcaatacttc tgacaagttc ttagtttatg gatctattga aggtgaatct    1860
gatatttcag gaataattgt ccttcttgac tttgcttctc ttcatcctcg cgattgctaa    1920
ggttatgaaa accctgacac ttctgattct gattatgaat actggactcc tcataatccc    1980
agtgaattct gttttattagg acgtgaaatt aaatatgtca gaagaaaaag agatgctgct    2040
tgctttaatc ccgaaacttt tgaaagatct tatgttgtta gaaaatgtga atgtactgaa    2100
cttgattggg aatgtgatgt cggatttgct cgtgctaaag acgatagcaa agaaagaact    2160
ggcccttgcg ttccttttaaa agacttcaaa gtggattaca atcctccata aacttgcagt    2220
ggctcttacc aagttacata aggttacaga agagtagctg gtaattaatg tataggcggt    2280
attgatcatg ctccaattta ataccttgt cctatgtttg gcttcttgag ctataacaac    2340
cttttcacca atgttcttat tttaggagct atggctggtg ttttctactt aattatataa    2400
aataaagaag tagtaataac atttgtagct acatcaaatc ttgatgccta cattaactta    2460
ggtaaaactt acctaagaa gggttatact tttgttacat caattgtcct tccacaagct    2520
tcaaattaat aataaggata tttccaagct aaccaagatg aggaaaatag aaaatctcat    2580
tccttaaagg atcaacatca ttaattccat gataatttaa ttgaaagcca tgatcatgat    2640
gatgaggaag agtaaagtga tgcagtataa taataattaa cttcttctta agtcccttaa    2700
aataatagta acaaaaacaa taataatagt aatacaccaa actaagctca gcacaaagat    2760
cttcttgatg aacatgatgg tgaagaagat cctttttgatc ctagaaattg aaaaataatt    2820
gactgaataa tattgctaat ttatttttttt acttaaataa taaatataa aaaataaata    2880 aattaatttt tgtcttcat taatattatt tagaaagttt ttctaagtaa tttaatatag    2940
tgtgtcaagt atctttttct cttaacttat gtatttatc aaatcctttt ttactttatt    3000
attcctagtt                                                             3010
```

<210> SEQ ID NO 7
<211> LENGTH: 872
<212> TYPE: PRT
<213> ORGANISM: Tetrahymena thermophila

<400> SEQUENCE: 7

Met Lys Lys Gln Asp Leu Thr Val Tyr Val Ala Ala Phe Leu Leu Leu
1               5                   10                  15

Phe Ser Cys Val Ile His Phe Ala Asn Ala Gln Asp Lys Val Ser Glu
            20                  25                  30

Ile Phe Lys Asp Lys Tyr Asp Val Lys Tyr Arg Val Thr Glu Leu Asp
        35                  40                  45

Ser Pro Val Gln Glu Ile Leu Trp Cys Gly Ser Ser Gln Ala Thr Ser
    50                  55                  60

```
Glu Asp Gly Asp Ile Ile Thr Tyr Asp Gln Thr Ala Lys Val Arg Lys
 65                  70                  75                  80

Leu Tyr Val Leu Thr Asp Lys Gly Lys Leu Tyr Tyr Ser Glu Asp Tyr
                 85                  90                  95

Gly Ile Thr Leu Lys Leu Ile Asn Asp Ile Arg Gln Ser Thr Asn
            100                 105                 110

Ser Lys Gln Thr Gln Val Glu Val Asp Asp Ile Met Ile Ser Pro Val
            115                 120                 125

Lys Asn Arg Lys Val Phe Ile Phe Thr Lys Ser Gly Glu Ser Tyr Tyr
        130                 135                 140

Thr Glu Asn Cys Gly Ala Thr Tyr Thr Ser Phe Lys His Glu Ile Leu
145                 150                 155                 160

Leu Tyr Asp Ile Gln Pro Asn Pro Ser Asp His Lys Ser Leu Ile Gly
                165                 170                 175

Leu Val Pro Val Gln Cys Gln Lys Gly Asp Pro Glu Cys Gln Gly Gly
            180                 185                 190

Asp Ser Asp Leu Tyr Leu Thr Val Asp Ser Gly Met Thr Trp Arg Lys
        195                 200                 205

Ile Val Ser Asn Val Asn Gln Ala Gln Trp Asp Lys Thr Lys Gln Thr
210                 215                 220

Leu Met Asn Thr Gln Asn Arg Ile Ile Leu Ser His Gln Glu Gln Glu
225                 230                 235                 240

Lys Asn Glu Lys Gly Glu Asn Val Phe Leu Asn Lys Val Ser Tyr Thr
                245                 250                 255

Asp Asn Tyr Gly Lys Asp Leu Lys Val Val Glu Lys Asn Gly Val Arg
            260                 265                 270

Phe Tyr Gln Thr Glu Glu Tyr Ile Phe Val Leu Ile Gln Gly Lys Glu
        275                 280                 285

Phe Gly Lys Tyr Lys Leu Asn Ile Gly Pro Ser Phe Val Thr Gln Ser
    290                 295                 300

Ser Ser Arg Lys Glu Ile Asp Leu Pro Leu Gln Arg Val Lys Asp Glu
305                 310                 315                 320

Ser Phe Thr Val Leu Asp Ile Asp Ala Gly Gln Ile Leu Ile Ala Ile
                325                 330                 335

Asn His Glu Gly Asp Ser Ala Gly Tyr Thr Asn Val Tyr Ile Ser Asn
            340                 345                 350

Ser Gln Gly Glu Gln Phe Thr Leu Ser Leu Gln Tyr Thr Val Gly Asp
        355                 360                 365

Asp Asp Ser Asn Ile Asp Phe Glu Pro Ile Asn Ser Asn Glu Gly Val
    370                 375                 380

Tyr Ile Ala Asn Thr Tyr Thr Ala Ala Ser Ile Ser Lys Tyr Gln Lys
385                 390                 395                 400

Leu Leu Gln Arg Lys Glu Gly Gln Lys Ser Ser Gly Ser Ser Leu Thr
                405                 410                 415

Leu Asp Ser Phe Lys Ile Glu Asn Met Lys Lys Thr Lys Ile Thr Phe
            420                 425                 430

Asn Lys Gly Gly Asp Trp His Ala Ile Lys Ala Pro Glu Phe Asn Tyr
        435                 440                 445

Ala Gly Asn Pro Ile Arg Cys Ser Gly Asp Cys Ser Leu Asn Phe Lys
    450                 455                 460

Gly Arg Thr Glu Ser Gln Gly Thr Pro Val Tyr Ser Thr Asp Asn Ala
465                 470                 475                 480

Pro Gly Ile Ile Leu Ala Thr Gly Asn Val Gly Ser Tyr Leu Thr Asn
```

```
                    485                 490                 495
Asn Gln Asp Glu Leu Arg Thr Tyr Leu Ser Ile Asp Gly Gly His Thr
                500                 505                 510

Trp Lys Glu Ile Gln Val Gly Ser His Glu Tyr Glu Ile Gly Asp Gln
                515                 520                 525

Gly Gly Ile Ile Ala Met Ala Arg Asp Asp Lys Leu Thr Asn Glu Val
                530                 535                 540

Ile Tyr Ser Val Asp Glu Gly Glu Thr Trp Arg Lys Leu Asn Phe Lys
545                 550                 555                 560

Asp Glu Asn Lys Phe Lys Val Asp Ser Phe Val Thr Glu Glu Gly Asn
                565                 570                 575

Asp Glu Arg Thr Phe Leu Phe Tyr Gly Thr Lys Thr Gly Ala Asp Gly
                580                 585                 590

Asn Thr Lys Gly Val Ile Gly Ala Ile Asn Phe Ser Asn Leu Phe Lys
                595                 600                 605

Lys Glu Cys Thr Gly Phe Glu Asn Pro Gly Glu Asp Gly Ser Asp Tyr
                610                 615                 620

Glu Arg Trp Val Pro Leu Asn Phe Glu Gly Lys Lys Cys Leu Phe Gly
625                 630                 635                 640

Ser Lys Ile Ser Tyr Ile Arg Lys Lys Thr Asp Ser Ser Cys Phe Asn
                645                 650                 655

Asn Arg Lys Val Gly Asp Leu Arg Met Val Gln Gly Ser Cys Glu Cys
                660                 665                 670

Thr Glu Glu Asp Phe Glu Cys Asp Tyr Gly Phe Thr Lys Asp Leu Ile
                675                 680                 685

Asp Glu Thr Lys Cys Val Pro Ile Asn Ala Lys Phe Ala Lys Lys Arg
                690                 695                 700

Asp Gln Pro Pro Leu Asn Cys Lys Asp Phe Tyr Phe Val Ser Ser Gly
705                 710                 715                 720

Lys Arg Lys Ile Ala Asn Asn Gln Cys Gln Gly Gly Ile Glu Glu Leu
                725                 730                 735

Tyr Thr Lys Lys Lys Val Arg Cys Pro Gly Asn Glu Glu Ala Gln Gln
                740                 745                 750

Thr Gln Gln Gln Thr Gln Asn Thr Gln Ala Asn Thr Ala Gln Asn Asn
                755                 760                 765

Gln Gln Asp Leu Phe Ser Arg Lys Pro Glu Asp Ile Lys Lys Glu Ile
                770                 775                 780

Lys Glu Gln Tyr Gly Asn Gln Thr Asp Gln Thr Ser Gly Ile Ser Phe
785                 790                 795                 800

Leu Gly Val Leu Ala Ala Phe Leu Val Leu Phe Leu Leu Tyr Thr Tyr
                805                 810                 815

Arg Val Glu Ile Leu Ser Lys Ile Lys Glu Tyr Gln Gln Asn Gln Lys
                820                 825                 830

Asn Lys Lys Gly Asp Asn Asn Lys Tyr Gly Tyr Lys Gln Lys Ser Tyr
                835                 840                 845

Gly Asn Asn Ala Glu Gln Tyr Ser Leu Phe Gln Asn Asp Gln Asp Asn
                850                 855                 860

Asp Glu Tyr Asp Ala Asp Met Leu
865                 870

<210> SEQ ID NO 8
<211> LENGTH: 2689
<212> TYPE: DNA
<213> ORGANISM: Tetrahymena thermophila
```

<400> SEQUENCE: 8

```
gaaattacaa aaagcaatct ttttagagta gcatttaaaa taaattataa attaggtatt    60
tgtttagatt atgaaaaaat aagatctgac agtatatgtt gcagctttcc tgcttctctt   120
ttcttgtgtt attcactttg ctaatgctca agataaagtt agtgaaattt ttaaagacaa   180
atatgatgtc aaatatagag taactgaatt agattcacct gtttaggaaa ttctatggtg   240
cggtagttct taagcaacat ctgaagacgg agatattatc acctatgatt aaacagcaaa   300
agttagaaaa ctttatgtct taactgataa aggtaaattg tattactcag aagactatgg   360
cattacattg aagttgatta atgatgatat ccgtcaatca accaattcca aataaactta   420
ggtcgaagtc gatgatatca tgatctcacc tgttaaaaat agaaaagtgt tcatcttcac   480
taaaagcggt gaaagctatt atacagaaaa ctgtggtgcc acttatactt ctttcaagca   540
cgagattctc ctatacgata tctagcccaa tccttctgat cacaagtctt tgataggact   600
tgtacccgtt tagtgctaaa aaggagatcc tgagtgctaa ggtggtgatt ctgatttata   660
cttaacagta gatagcggta tgacttggag aaaaatagtc tctaacgtaa atcaagcata   720
gtgggataag accaaataaa ctctcatgaa cacataaaat agaattattt tgtctcatta   780
agagtaagaa aagaatgaaa aaggagaaaa tgtattcctc aataaagtaa gctacactga   840
taactatggt aaagatttaa aagtggtaga aaagaatgga gttagattct attaaacaga   900
agaatatatt tttgttttaa tctaaggaaa ggaatttggc aaatataaac ttaatattgg   960
accttctttt gttactcaat cttctagcag aaaagagatc gatttacctc tttaaagagt  1020
taaagatgaa tcttttactg tcttggacat agatgcaggc taaattctta tcgctattaa  1080
tcatgaaggt gacagtgctg gatacactaa tgtttacatt tcaaactcct aaggagaata  1140
gttcactctt tcacttcaat atacagtagg tgatgatgat tctaacattg attttgaacc  1200
cattaacagc aacgaaggag tttatattgc aaacacatac actgcagctt caatttcaaa  1260
atatcaaaag cttttgcaaa gaaaagaagg acaaaaatct tctggatctt cactcacttt  1320
ggattcattt aaaattgaaa atatgaaaaa aactaaaatt acatttaaca agggtggtga  1380
ctggcacgca atcaaggctc ccgaattcaa ttatgctgga atcctattc gttgctctgg  1440
tgactgttct cttaacttta aaggaagaac tgagtctcaa ggtactccag tctattctac  1500
tgataatgct cctggtatta ttttggctac aggtaatgtt ggctcttatc tcactaataa  1560
tcaagatgaa ttaagaactt atctttctat tgatggtgga cacacatgga aagagattca  1620
agttggatct catgaatacg aaattggtga ttaaggcggt atcatcgcta ggctagaga  1680
cgataagctt acaaacgaag ttatttactc tgttgatgaa ggagaaacat ggagaaaatt  1740
gaatttcaag gatgaaaata aatttaaagt agatagtttt gttacagaag aaggcaacga  1800
tgaaagaact ttcttgttct atggaaccaa gactggtgca gatggaaata ctaaaggtgt  1860
aattggtgct atcaactttt caaatttatt caaaaaggaa tgcacaggat ttgaaaaccc  1920
tggcgaagat ggcagtgatt atgagagatg ggtcccatta aactttgaag gaaaaaaatg  1980
cttatttggt tcaaaaattt catacataag aaaaaaaact gattctagtt gctttaacaa  2040
cagaaaagtt ggtgatttaa gaatggtcta aggatcttgt gaatgtacag aagagatttt  2100
cgaatgtgat tatggtttca ctaaagattt aattgatgaa acaaaatgtg ttccaataaa  2160
tgcaaaattt gcaagaaaaa gagactaacc acctttgaac tgcaaagatt tttactttgt  2220
ttcttcagga aaaagaaaaa ttgcaaacaa ctaatgttaa ggcggtattg aagaattata  2280
```

```
tacaaagaaa aaagtaagat gcccaggaaa tgaagaagct cagcaaactt agcaataaac    2340
tcaaaatact taagctaata cagcttaaaa taactagtaa gacttattta gcagaaagcc    2400
agaagatata aaaaagaaa taaaagaata atatggcaat taaacagatt agacatcagg     2460
aatatccttc ctcggtgttt tggcagcttt cttagtatta ttcttattat atacttacag    2520
ggtagaaata cttagcaaga taaagaata tcaataaaac caaagaaca aaagggtga       2580 taacaataaa tatggctata agcaaaaatc ctatggaaat aatgctgaac agtattcact    2640
tttctaaaat gatcaagaca atgatgaata cgatgcagat atgctttga               2689
```

<210> SEQ ID NO 9
<211> LENGTH: 6277
<212> TYPE: DNA
<213> ORGANISM: Artificial Sequence
<220> FEATURE:
<223> OTHER INFORMATION: Synthetic DNA Construct

<400> SEQUENCE: 9

```
ttgtaagcgt taatattttg ttaaaattcg cgttaaattt ttgttaaatc agctcatttt     60
ttaaccaata ggccgaaatc ggcaaaatcc cttataaatc aaaagaatag accgagatag    120
ggttgagtgt tgttccagtt tggaacaaga gtccactatt aaagaacgtg gactccaacg    180
tcaaagggcg aaaaaccgtc tatcagggcg atggcccact acgtgaacca tcaccctaat    240
caagtttttt ggggtcgagg tgccgtaaag cactaaatcg aaccctaaa gggagccccc     300 gatttagagc ttgacgggga agccggcga acgtggcgag aaaggaaggg aagaaagcga    360
aaggagcggg cgctagggcg ctggcaagtg tagcggtcac gctgcgcgta accaccacac    420
ccgccgcgct taatgcgccg ctacagggcg cgtcccattc gccattcagg ctgcgcaact    480
gttgggaagg gcgatcggtg cgggcctctt cgctattacg ccagctggcg aaaggggggat   540 gtgctgcaag gcgattaagt tgggtaacgc cagggttttc ccagtcacga cgttgtaaaa    600
cgacggccag tgaattgtaa tacgactcac tatagggcga attgggtacc gggcccccc    660 tcgaggtcga cggtatcgat aagctctgat tgttaaatgt tgaaagagta tttttatgag   720
aagtattttt tgttttgaaa tcagaaattt tattcctctt ttttagtaaa atacttaat     780 tgttatttat gtaacaaatg taataaaatc gcaaatgaaa tattcttttt aaccaattaa   840
ataaataata ctattttaa ttaaaatgat gagcatatta atttaaaaat ggatcttttt     900
aattaatgtt aaattataat atttaacaat aaaaaatatg ctgttgatat tttaataaat   960
tcgcaatcaa gaaattattg attttattat ttctattaat aatatttatt aattaattat  1020
ttaatgtaga aataaataaa taaattatga agaaaataa aatattaga caagatagat    1080 tgatagaaaa caaaaaataa ttagtgaaaa catttttagtt taaaacaaa ttaataagac   1140 tgtttattta acaaatattc agtagttagt ttgttagtta gtattgtatt cattttattt   1200
tgtaaaatga ttgattacat taaaattaat aatcattaat taattaattg cttatgctct   1260
caagtaattt tttaatgata agcttgatat cgaattcaga tcccccgggc tgcatttttc   1320
cagtaaaaat ttgaaaattt aatggcaaaa aaaatatta ttattggatt tgcagacaaa   1380
tttttaagag ctaacatgta tgtgaagagg aatttttttt tttagaaagt taaaaaaaat   1440
aattgacata aaatatatat acaaatgagt tgtaaaataa tgatttttagt caatttggaa  1500 taaattatat tttatagtag tatattaaca cgttttttg gtgctttaat gttaatataa    1560
tacactaaaa attaattttta tataatatat ttattttata tgaaagtttg taaatatata  1620
ttgaattttt aatttaagga tctcagaaga attcgtcaag aagacgatag aaggcgatac   1680
```

```
gttgagaatc gggagcggcg ataccgtaaa ggacaaggaa acggtcagcc cattcaccac    1740
caagttcttc agcaatatca cgggtagcta aggcaatatc ttgataacgg tcggcgacac    1800
caagacgacc acagtcgatg aaaccagaaa acgaccatt  ttcaaccatg atattgggta    1860
agcaggcatc accatgggtg acgacaagat cttcaccgtc gggcatacgg gccttaagtc    1920
tggcgaaaag ttcggcaggg gcaagacctt gatgttcttc gtcaagatca tcttgatcga    1980
caagaccggc ttccatacga gtacgagcac gttcgatacg atgtttggct tggtggtcga    2040
aagggcaggt agcgggatca agggtatgaa gacgacgcat agcatcagcc atgatagaaa    2100 cttttttcggc aggagcaagg tgagaagaaa gaagatcttg accggggact tcacctaaaa    2160
gaagccagtc tctaccggct tcagtgacaa cgtcaaggac agcagcgcaa ggaacaccgg    2220
tggtggcaag ccaagaaaga cgggcagctt catcttgaag ttcattaagg caccagaaa     2280 ggtcggtctt gacgaaaaga acaggacgac cttgagcaga aagacggaag acggcggcat    2340
cagagcaacc gatggtttgt tgagcccagt cataaccgaa aagtctttcg acccaagcgg    2400
cgggagaacc agcgtgtaaa ccatcttgtt caatcattat tttaagttta gtattattat    2460
ttattttatt agagctttat taaattttt taattttttt aaattatata agaataaaa      2520 aagacgaata tatatata cactatttac attatttat atggatcatt gtataaatcg       2580
tgaatcacgt agctaagaat tatatcagaa atataaaaa ttactttata ttcaagagag     2640
attcaagaat cacatctata ttttagaata gaagaatttt gaaaattagt taggttgact    2700
catgatttaa atcatgagtc aatcaattta tatttttat cagaaataaa aagatttaca    2760
aataattcat gacacaaaat tcaagaatca caacttaata ttaaaatata atagaaacgg    2820
ataattgaaa ataaaaaata aatgatagcc taaataatga gtaatatttt gaaaattaat    2880
gattcacata ttataattga tgaatgagct atgttttgag cagcttatat atttaataaa    2940
taaaataatt gatatttatc tattttatat ttcatgtttt cttaaaaaa catgtcatct     3000 tttttatcaa tatatttgaa atttaaagaa ataattgaa taaacgatac aatatatttt     3060
aagatatata aaaagttttt gctttcaaga tattaaaaat agtgatataa aaaataagta    3120
ctctattatg tttttttctta ttcagtatta tacctttaat cattattatc tttttattta    3180 ttttagtta gttattttt atttttatga atatttaaag agctaaaaaa aatttaaaaa      3240
tgtgtattta aattaaagga gttattcaaa acccttatta tttttatttt ttaaatattt    3300
tttagaaata aattgtatat cgaattcctg cagctaaaaa gattgctttt tgtaatttct    3360 atgatttttaa gagtatttt taattaata ttttatat ttaattaatt atgattttt        3420 tttttttttg atgagaagat acacttatt aaataacata gttcgaaata tcataatcaa     3480
cttcttttaa aaaatttttt ttaagaatca acaaactct ctaacataca cgcattcgct     3540
catttattaa aattttacg ttttgcaaat ttaatttgtt ggcacttttg tatcttcact     3600
caattaccaa aattttctct caattttcct tccttttata aaataaccaa tgataatttt    3660
tgatccaata cgttttaaaa tttagtcttt cttttaaaat aataacaaag aaagataaat    3720
acatgagtaa aaataaaaaa agcagatagc tatgcaattt attaattttt ttgaaattta    3780
taaatatttt tggagatatt ttttcattat agtgattaaa attaatttta tttagaaaaa    3840
tcaagtttta tttatgaata aacagttatt tacttaagat tttgttttca ctattagtat    3900
tctgttttaa atctttaagt atttttcttag ttaacaatct tacaatcctt attttgattg    3960
ctatttaaaa ttaaaatatt ttaaatagaa catttaacat aacagatatg aaaataaaca    4020
```

```
gcgttttacg ctagcgcatg ctctagagcg gccgccaccg cggtggagct ccagcttttg     4080 ttcccttag tgagggttaa tttcgagctt ggcgtaatca tggtcatagc tgtttcctgt      4140
gtgaaattgt tatccgctca caattccaca acatacga gccggaagca taaagtgtaa       4200
agcctggggt gcctaatgag tgagctaact cacattaatt gcgttgcgct cactgcccgc     4260
tttccagtcg ggaaacctgt cgtgccagct gcattaatga atcggccaac gcgcggggag     4320
aggcggtttg cgtattgggc gctcttccgc ttcctcgctc actgactcgc tgcgctcggt     4380
cgttcggctg cggcgagcgg tatcagctca ctcaaaggcg gtaatacggt tatccacaga     4440
atcaggggat aacgcaggaa agaacatgtg agcaaaaggc cagcaaaagg ccaggaaccg     4500
taaaaaggcc gcgttgctgg cgttttttcca taggctccgc cccctgacg agcatcacaa     4560 aaatcgacgc tcaagtcaga ggtggcgaaa cccgacagga ctataaagat accaggcgtt     4620
tccccctgga agctccctcg tgcgctctcc tgttccgacc ctgccgctta ccggatacct     4680
gtccgccttt ctcccttcgg aagcgtggc gctttctcat agctcacgct gtaggtatct     4740
cagttcggtg taggtcgttc gctccaagct gggctgtgtg cacgaacccc ccgttcagcc     4800
cgaccgctgc gccttatccg gtaactatcg tcttgagtcc aacccggtaa gacacgactt     4860
atcgccactg gcagcagcca ctggtaacag gattagcaga gcgaggtatg taggcggtgc     4920
tacagagttc ttgaagtggt ggcctaacta cggctacact agaaggacag tatttggtat     4980
ctgcgctctg ctgaagccag ttaccttcgg aaaaagagtt ggtagctctt gatccggcaa     5040
acaaaccacc gctggtagcg gtggtttttt tgtttgcaag cagcagatta cgcgcagaaa     5100
aaaaggatct caagaagatc ctttgatctt ttctacgggg tctgacgctc agtggaacga     5160
aaactcacgt taagggattt tggtcatgag attatcaaaa aggatcttca cctagatcct     5220
tttaaattaa aaatgaagtt ttaaatcaat ctaaagtata tatgagtaaa cttggtctga     5280
cagttaccaa tgcttaatca gtgaggcacc tatctcagcg atctgtctat ttcgttcatc     5340
catagttgcc tgactccccg tcgtgtagat aactacgata cgggagggct taccatctgg     5400
ccccagtgct gcaatgatac cgcgagaccc acgctcaccg gctccagatt tatcagcaat     5460
aaaccagcca gccggaaggg ccgagcgcag aagtggtcct gcaactttat ccgcctccat     5520
ccagtctatt aattgttgcc gggaagctag agtaagtagt tcgccagtta atagtttgcg     5580
caacgttgtt gccattgcta caggcatcgt ggtgtcacgc tcgtcgtttg gtatggcttc     5640
attcagctcc ggttcccaac gatcaaggcg agttacatga tccccatgt tgtgcaaaaa      5700 agcggttagc tccttcggtc ctccgatcgt tgtcagaagt aagttggccg cagtgttatc     5760
actcatggtt atggcagcac tgcataattc tcttactgtc atgccatccg taagatgctt     5820
ttctgtgact ggtgagtact caaccaagtc attctgagaa tagtgtatgc ggcgaccgag     5880
ttgctcttgc ccggcgtcaa tacgggataa taccgcgcca catagcagaa ctttaaaagt     5940
gctcatcatt ggaaaacgtt cttcggggcg aaaactctca aggatcttac cgctgttgag     6000
atccagttcg atgtaaccca ctcgtgcacc caactgatct tcagcatctt ttactttcac     6060
cagcgtttct gggtgagcaa aacaggaag gcaaatgcc gcaaaaaagg gaataagggc       6120
gacacggaaa tgttgaatac tcatactctt ccttttcaa tattattgaa gcatttatca      6180
gggttattgt ctcatgagcg gatacatatt tgaatgtatt tagaaaaata aacaaatagg     6240
ggttccgcgc acatttcccc gaaaagtgcc acctaaa                              6277
```

<210> SEQ ID NO 10
<211> LENGTH: 6648

<212> TYPE: DNA
<213> ORGANISM: Artificial Sequence
<220> FEATURE:
<223> OTHER INFORMATION: Synthetic DNA Construct

<400> SEQUENCE: 10

```
cacctaaatt gtaagcgtta atattttgtt aaaattcgcg ttaaattttt gttaaatcag      60
ctcattttt aaccaatagg ccgaaatcgg caaatccct tataaatcaa agaatagac       120
cgagataggg ttgagtgttg ttccagtttg aacaagagt ccactattaa agaacgtgga     180
ctccaacgtc aaagggcgaa aaaccgtcta tcagggcgat ggcccactac gtgaaccatc    240
accctaatca gtttttttgg ggtcgaggtg ccgtaaagca ctaaatcgga accctaaagg    300
gagcccccga tttagagctt gacggggaaa gccggcgaac gtggcgagaa aggaagggaa    360
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tgggtaccgg    660
gccccccctc gaggtcgacg gtatcgataa gcttgattta cgacaaattc aatatgccat    720
ttcaaaagta atctgagttt ctggaagttt aatagaataa aaattacaga attgatattt    780
aaatcaaaat tttcaagcta aattagattg attttttaagt tactcaaata ataaaggtag    840
taaataaaat caattttctc aaacaataat tatcttctac ataaaactgc tttcttaata    900
cccctaatta aaaagatat attttttgaaa atttaaacaa aatttggaag aaaaattaat    960
ttcatttgat aaattttatt taagtaggt tctccataac taaccctcc cctaatcaaa   1020
tatttgtaaa agctttgggt ttttttctaa aaaattttca aaatttattt ttttcaaaac   1080
atatttatta tttcaagtta aacattttgt gaatttaatg atttataaaa actcaaaaaa   1140
atagttgttt agaattatta tttagcttta tttgttatat tattaagata tattacattt   1200
tgcctttat aaattaaata cgcatttcac aaaagactgt tcatttataa gattattcat    1260
caatatatta atatattatt ttttgctatt ttttaattt ggttatttaa aattctagaa    1320
tcatgattaa gtatttattt ttaattatct tgattataaa taatctaaat ttttatgtta    1380
actaaaaatc tttggtagta aataaataaa ttattattat tattattaaa aaatcaatac    1440
tattaaaatt atttttaaat taaattaatc tacaaagaaa tttatgaaaa aacaaaaaat    1500
caattagtta attaagcttg atatcgaatt cagatccccc gggctgcatt tttccagtaa    1560
aaatttgaaa atttaatggc aaaaaaaaat attattattg gatttgcaga caaatttta    1620
agagctaaca tgtatgtgaa gaggaatttt ttttttttaga aagttaaaaa aataattga   1680
cataaaatat atatacaaat gagttgtaaa ataatgattt tagtcaattt ggaataaatt    1740
atatttata gtagtatatt aacacgttttt tttggtgctt taatgttaat ataatacact    1800
aaaaattaat tttatataat atatttattt tatatgaaag tttgtaaata tatattgaat    1860
ttttaattta aggatctcag aagaattcgt caagaagacg atagaaggcg atacgttgag    1920
aatcgggagc ggcgataccg taaggacaa ggaaacggtc agcccattca ccaccaagtt    1980
cttcagcaat atcacgggta gctaaggcaa tatcttgata acggtcggcg acaccaagac    2040
gaccacagtc gatgaaacca gaaaacgac cattttcaac catgatattg ggtaagcagg    2100
catcaccatg ggtgacgaca agatcttcac cgtcgggcat acgggcctta agtctggcga    2160
```

-continued

```
aaagttcggc agggggcaaga ccttgatgtt cttcgtcaag atcatcttga tcgacaagac   2220
cggcttccat acgagtacga gcacgttcga tacgatgttt ggcttggtgg tcgaaagggc   2280
aggtagcggg atcaagggta tgaagacgac gcatagcatc agccatgata gaaactttt   2340 cggcaggagc aaggtgagaa gaagaagat cttgaccggg gacttcacct aaaagaagcc   2400
agtctctacc ggcttcagtg acaacgtcaa ggacagcagc gcaaggaaca ccggtggtgg   2460
caagccaaga aagacgggca gcttcatctt gaagttcatt aagggcacca gaaaggtcgg   2520
tcttgacgaa aagaacagga cgaccttgag cagaaagacg gaagacggcg gcatcagagc   2580
aaccgatggt ttgttgagcc cagtcataac cgaaaagtct ttcgacccaa gcggcgggag   2640
aaccagcgtg taaaccatct tgttcaatca ttattttaag tttagtatta ttatttattt   2700
tattagagct ttattaaatt tttttaattt ttttaaatta tataaagaat aaaaaagacg   2760
aatatatata tatacactat ttacattatt ttatatggat cattgtataa atcgtgaatc   2820
acgtagctaa gaattatatc agaaatataa aaaattactt tatattcaag agagattcaa   2880
gaatcacatc tatattttag aatagaagaa ttttgaaaat tagttaggtt gactcatgat   2940
ttaaatcatg agtcaatcaa tttatatttt ttatcagaaa taaaaagatt tacaaataat   3000
tcatgacaca aaattcaaga atcacaactt aatattaaaa tataatagaa acggataatt   3060
gaaaataaaa aataaatgat agcctaaata atgagtaata ttttgaaaat taatgattca   3120
catattataa ttgatgaatg agctatgttt tgagcagctt atatatttaa taaataaat   3180 aattgatatt tatctatttt atatttcatg ttttctttaa aaacatgtc atctttttta   3240 tcaatatatt tgaaatttaa agaaaataat tgaataaacg atacaatata ttttaagata   3300
tataaaaaag ttttgctttc aagatattaa aaatagtgat ataaaaaata agtactctat   3360
tatgtttttt cttattcagt attataccet taatcattat tatctttta tttattttta   3420 gttagttatt ttttattttt atgaatattt aaagagctaa aaaaaattta aaaatgtgta   3480
tttaaattaa aggagttatt caaaacccctt attattttt attttaaat attttttaga   3540 aataaattgt atatcgaatt cctgcagaaa gatatttaat cacttaataa ctaagtctgt   3600
ttctcatgcc aagaaaaatt caactaacaa taagtttatc aaaaattttc tatttagatg   3660
tagaaaagaa aaagaaaaaa caaatctaaa ggttattagc atatttttc ttcttaaaca   3720 aggattaatt tttacgtttt taaatttcag accaatcaat caatcatgaa tgataataga   3780 tattttaaa atatagcttt aaaaaaatac aatatttaac gagattataa tatttttttt   3840
taatactaaa attcttcgct ttgctgagca atttgatttg aaaaagctaa tcaacttat   3900 taatttttt cggattaggt ttttaaaatt ttataaggaa taaacgtttt ttaatgatat   3960
gctatttagg atactgcttt tttaaagtaa tttttaatt tagatttaag tttactctaa   4020
caataaggat ttaaatataa acaatttaca aataatttta tatagattag aattttaatt   4080
tatttattta tttacttatt aatttaagtt aaattattta atttgattta actaaaattt   4140
attttgaagt tatattacaa aatttcatt ttatgttaaa ctcagttagt ttgatcattg   4200
tttcatacat ctgattaaat attttaatat gatgaggaac caaacttgtg actttaatta   4260
tttgaattaa taaaaaaatt ctgcatatcg ttgctgtctt attttaagtt tagctttaca   4320
ttatataaaa gactatctat tggttggtat tactattatt tattatttaa taatgatgtt   4380
atttactagc tgcctaatcc agactgaggc tagcgcatgc tctagagcgg ccgccaccgc   4440
ggtggagctc cagcttttgt tccctttagt gagggttaat ttcgagcttg gcgtaatcat   4500
ggtcatagct gtttcctgtg tgaaattgtt atccgctcac aattccacac aacatacgag   4560
```

```
ccggaagcat aaagtgtaaa gcctggggtg cctaatgagt gagctaactc acattaattg    4620
cgttgcgctc actgcccgct ttccagtcgg gaaacctgtc gtgccagctg cattaatgaa    4680
tcggccaacg cgcggggaga ggcggtttgc gtattgggcg ctcttccgct tcctcgctca    4740
ctgactcgct gcgctcggtc gttcggctgc ggcgagcgg atcagctcac tcaaaggcgg     4800
taatacggtt atccacagaa tcaggggata cgcaggaaa gaacatgtga gcaaaaggcc    4860
agcaaaaggc caggaaccgt aaaaaggccg cgttgctggc gttttccat aggctccgcc    4920
cccctgacga gcatcacaaa aatcgacgct caagtcagag gtggcgaaac ccgacaggac    4980
tataaagata ccaggcgttt ccccctggaa gctccctcgt gcgctctcct gttccgaccc    5040
tgccgcttac cggatacctg tccgcctttc tcccttcggg aagcgtggcg ctttctcata    5100
gctcacgctg taggtatctc agttcggtgt aggtcgttcg ctccaagctg ggctgtgtgc    5160
acgaaccccc cgttcagccc gaccgctgcg ccttatccgg taactatcgt cttgagtcca    5220
acccggtaag acacgactta tcgccactgg cagcagccac tggtaacagg attagcagag    5280
cgaggtatgt aggcggtgct acagagttct tgaagtggtg gcctaactac ggctacacta    5340
gaaggacagt atttggtatc tgcgctctgc tgaagccagt taccttcgga aaaagagttg    5400
gtagctcttg atccggcaaa caaaccaccg ctggtagcgg tggttttttt gtttgcaagc    5460
agcagattac gcgcagaaaa aaaggatctc aagaagatcc tttgatcttt tctacggggt    5520
ctgacgctca gtggaacgaa aactcacgtt aagggatttt ggtcatgaga ttatcaaaaa    5580
ggatcttcac ctagatcctt ttaaattaaa aatgaagttt taaatcaatc taagtatat     5640
atgagtaaac ttggtctgac agttaccaat gcttaatcag tgaggcacct atctcagcga    5700
tctgtctatt tcgttcatcc atagttgcct gactccccgt cgtgtagata actacgatac    5760
gggagggctt accatctggc cccagtgctg caatgatacc gcgagaccca cgctcaccgg    5820
ctccagattt atcagcaata aaccagccag ccggaagggc cgagcgcaga agtggtcctg    5880
caactttatc cgcctccatc cagtctatta attgttgccg ggaagctaga gtaagtagtt    5940
cgccagttaa tagtttgcgc aacgttgttg ccattgctac aggcatcgtg gtgtcacgct    6000
cgtcgtttgg tatggcttca ttcagctccg gttcccaacg atcaaggcga gttacatgat    6060
cccccatgtt gtgcaaaaaa gcggttagct ccttcggtcc tccgatcgtt gtcagaagta    6120
agttggccgc agtgttatca ctcatggtta tggcagcact gcataattct cttactgtca    6180
tgccatccgt aagatgcttt tctgtgactg gtgagtactc aaccaagtca ttctgagaat    6240
agtgtatgcg gcgaccgagt tgctcttgcc cggcgtcaat acgggataat accgcgccac    6300
atagcagaac tttaaaagtg ctcatcattg gaaaacgttc ttcggggcga aaactctcaa    6360
ggatcttacc gctgttgaga tccagttcga tgtaacccac tcgtgcaccc aactgatctt    6420
cagcatcttt tactttcacc agcgtttctg ggtgagcaaa aacaggaagg caaaatgccg    6480
caaaaaaggg aataagggcg acacggaaat gttgaatact catactcttc ctttttcaat    6540
attattgaag catttatcag ggttattgtc tcatgagcgg atacatattt gaatgtattt    6600
agaaaaataa acaaataggg gttccgcgca catttccccg aaaagtgc                 6648
```

<210> SEQ ID NO 11
<211> LENGTH: 6681
<212> TYPE: DNA
<213> ORGANISM: Artificial Sequence
<220> FEATURE:
<223> OTHER INFORMATION: Synthetic DNA Construct

```
<400> SEQUENCE: 11
cacctaaatt gtaagcgtta atattttgtt aaaattcgcg ttaaattttt gttaaatcag      60
ctcatttttt aaccaatagg ccgaaatcgg caaaatccct tataaatcaa agaatagac      120 cgagataggg ttgagtgttg ttccagtttg aacaagagt ccactattaa agaacgtgga     180
ctccaacgtc aaagggcgaa aaaccgtcta tcagggcgat ggcccactac gtgaaccatc     240
accctaatca agttttttgg ggtcgaggtg ccgtaaagca ctaaatcgga accctaaagg     300
gagcccccga tttagagctt gacggggaaa gccggcgaac gtggcgagaa aggaagggaa     360
gaaagcgaaa ggagcgggcg ctagggcgct ggcaagtgta gcggtcacgc tgcgcgtaac     420
caccacaccc gccgcgctta atgcgccgct acagggcgcg tcccattcgc cattcaggct     480
gcgcaactgt tgggaagggc gatcggtgcg ggcctcttcg ctattacgcc agctggcgaa     540 aggggggatgt gctgcaaggc gattaagttg ggtaacgcca gggttttccc agtcacgacg     600
ttgtaaaacg acggccagtg aattgtaata cgactcacta tagggcgaat tgggtaccgg     660
gccccccctc gaggtcgacg gtatcgataa gctgaagata aattattgct tcaatcattt     720
gctcagctaa ttatattagc taatttctat caaagcattt gtaggaagac agagaaaaat     780
cacagtcttt aaataaaata acaaaaaatt tattaatttt aaaggcatca tagatttttg     840
atatatataa attatcacat cctctaacga gatcaacata attttaggcc tgttacagct     900
tatcaaagca gtaagagtta ttcccatcat ctattgatat aagatatatt agataagatt     960
cttttctatt attaactgca taatatttcc catattttc gttttttatc acctaaaagt     1020
attcattttt attttataaa agctagtcta ttatttaagc tatttatttt tcatttaaaa     1080
tatcatttta tacatttgtt gaaaaccctt aatccatatt tttataattt tttttttca     1140 aaatttctta tcaaaaattt tttaattaaa acaaattcct ttaaaaacat ttaacttaaa     1200
tttggaagta aattattaga aggtttgtta gaatatttc aaactaggaa aataaagta     1260 aaaaaggatt tgataaaata cataagttaa gagaaaaaga tacttgacac actatattaa     1320
attacttaga aaaactttct aaataatatt aatgaaagac aaaaattaat ttatttattt     1380
ttatttattt attatttaag taaaaaaata aattagcaat attattcagt caattatttt     1440
aagcttgata tcgaattcag atcccccggg ctgcattttt ccagtaaaaa tttgaaaatt     1500
taatggcaaa aaaaaatatt attattggat ttgcagacaa attttttaaga gctaacatgt     1560 atgtgaagag gaattttttt ttttagaaag ttaaaaaaaa taattgacat aaaatatata     1620
tacaaatgag ttgtaaaata atgattttag tcaatttgga ataaattata ttttatagta     1680
gtatattaac acgttttttt ggtgctttaa tgttaatata atacactaaa aattaattttt     1740 atataatata tttattttat atgaaagttt gtaaatatat attgaatttt taatttaagg     1800
atctcagaag aattcgtcaa gaagacgata gaaggcgata cgttgagaat cgggagcggc     1860
gataccgtaa aggacaagga aacggtcagc ccattcacca ccaagttctt cagcaatatc     1920
acgggtagct aaggcaatat cttgataacg gtcggcgaca ccaagacgac cacagtcgat     1980
gaaaccagaa aaacgaccat tttcaaccat gatattgggt aagcaggcat caccatgggt     2040
gacgacaaga tcttcaccgt cgggcatacg ggccttaagt ctggcgaaaa gttcggcagg     2100
ggcaagacct tgatgttctt cgtcaagatc atcttgatcg acaagaccgg cttccatacg     2160
agtacgagca cgttcgatac gatgtttggc ttggtggtcg aaagggcagg tagcgggatc     2220
aagggtatga agacgacgca tagcatcagc catgatagaa actttttcgg caggagcaag     2280
gtgagaagaa agaagatctt gaccggggac ttcacctaaa agaagccagt ctctaccggc     2340
```

```
ttcagtgaca acgtcaagga cagcagcgca aggaacaccg gtggtggcaa gccaagaaag      2400
acgggcagct tcatcttgaa gttcattaag ggcaccagaa aggtcggtct tgacgaaaag      2460
aacaggacga ccttgagcag aaagacggaa gacggcggca tcagagcaac cgatggtttg      2520
ttgagcccag tcataaccga aaagtctttc gacccaagcg gcgggagaac cagcgtgtaa      2580
accatcttgt tcaatcatta ttttaagttt agtattatta tttattttat tagagcttta      2640 ttaaatttt ttaatttttt taaattatat aaagaataaa aaagacgaat atatatat         2700 acactattta cattatttta tatggatcat tgtataaatc gtgaatcacg tagctaagaa      2760
ttatatcaga aatataaaaa attactttat attcaagaga gattcaagaa tcacatctat      2820
attttagaat agaagaattt tgaaaattag ttaggttgac tcatgattta aatcatgagt      2880
caatcaattt atatttttta tcagaaataa aaagatttac aaataattca tgacacaaaa      2940
ttcaagaatc acaacttaat attaaaatat aatagaaacg gataattgaa aataaaaaat     3000
aaatgatagc ctaaataatg agtaatattt tgaaaattaa tgattcacat attataattg      3060
atgaatgagc tatgttttga gcagcttata tatttaataa ataaaataat tgatatttat      3120
ctattttata tttcatgttt tctttaaaaa acatgtcatc ttttttatca atatatttga      3180
aatttaaaga aaataattga ataaacgata caatatattt taagatatat aaaaaagttt      3240
tgctttcaag atattaaaaa tagtgatata aaaaataagt actctattat gttttttctt      3300
attcagtatt ataccttaa tcattattat ctttttattt attttagtt agttattttt        3360 tatttttatg aatatttaaa gagctaaaaa aaatttaaaa atgtgtattt aaattaaagg      3420
agttattcaa aacccttatt attttttatt tttaaatatt ttttagaaat aaattgtata      3480
tcgaattcct gcagatctat tttttctctc aattattttc ttttcaagga tttgtttttt      3540
ttttgttggt tattctatta attaaggcaa gatgaatgct tctatcaaaa aaaatacgtt      3600
ttttgatttg taattttttc ctattgattt caattatgtt tttaaaatta agtcatattc      3660
ttgtttatca agtttcatca gtaattcaag ctcattaaaa tctttaaaaa aatctttcta      3720
aatagtttca attatactga agtgattcaa tcattttta atcaaaaata tatttcagtc      3780
aattataatt tcattcatca aaataaaatg agatatttct aaaactgatt cataatttta      3840
gaaaattctt taatataaaa agatacattt tttaacttaa taatattttg gcattacata      3900
gctaatacaa aaatatgatt aatacaataa tgtaaatcat aagattaata tattagtaaa      3960
acaaaacata aaatcaagta ctgaattgtt ttattaatat attattttag taaaaatact      4020
ttcaaaatat tttttgaact aaagttgtaa ctaattatta ttttaacacc gtaaaaaata      4080
aaaaagttta aagattttta aatattaaat aaactaacaa accatattca aatatattta      4140
aaaatagtaa aaactaaata ataaatattt cttaaattta tgcttcaaat aaaattttc       4200 aatcagttaa ctatttttat attcaattta ttagatgtga taaattatat aaattaattc      4260 tttgttttc atttgttaat tttttatttt gtttcagtaa atgatatctt ttaatttctt       4320
cattcaaatt ccttaaaact atataataag gacaaattaa actcataaat atattctcaa      4380
atagttatta attttatata tcataattct tctatacaat tatccaatca taaaagtgga      4440
agctagcgca tgctctagag cggccgccac cgcggtggag ctccagcttt tgttcccttt      4500
agtgagggtt aatttcgagc ttggcgtaat catggtcata gctgtttcct gtgtgaaatt      4560
gttatccgct cacaattcca cacaacatac gagccggaag cataaagtgt aaagcctggg      4620
gtgcctaatg agtgagctaa ctcacattaa ttgcgttgcg ctcactgccc gctttccagt      4680
```

```
cgggaaacct gtcgtgccag ctgcattaat gaatcggcca acgcgcgggg agaggcggtt      4740
tgcgtattgg gcgctcttcc gcttcctcgc tcactgactc gctgcgctcg gtcgttcggc      4800
tgcggcgagc ggtatcagct cactcaaagg cggtaatacg gttatccaca gaatcagggg      4860
ataacgcagg aaagaacatg tgagcaaaag gccagcaaaa ggccaggaac cgtaaaaagg      4920
ccgcgttgct ggcgtttttc cataggctcc gcccccctga cgagcatcac aaaaatcgac      4980
gctcaagtca gaggtggcga aacccgacag gactataaag ataccaggcg tttccccctg      5040
gaagctccct cgtgcgctct cctgttccga ccctgccgct taccggatac ctgtccgcct      5100
ttctcccttc gggaagcgtg gcgctttctc atagctcacg ctgtaggtat ctcagttcgg      5160
tgtaggtcgt tcgctccaag ctgggctgtg tgcacgaacc ccccgttcag cccgaccgct      5220
gcgccttatc cggtaactat cgtcttgagt ccaacccggt aagacacgac ttatcgccac      5280
tggcagcagc cactggtaac aggattagca gagcgaggta tgtaggcggt gctacagagt      5340
tcttgaagtg gtggcctaac tacggctaca ctagaaggac agtatttggt atctgcgctc      5400
tgctgaagcc agttaccttc ggaaaaagag ttggtagctc ttgatccggc aaacaaacca      5460
ccgctggtag cggtggtttt tttgtttgca agcagcagat tacgcgcaga aaaaaggat      5520 ctcaagaaga tcctttgatc ttttctacgg gtctgacgc tcagtggaac gaaaactcac      5580
gttaagggat tttggtcatg agattatcaa aaaggatctt cacctagatc cttttaaatt      5640
aaaaatgaag ttttaaatca atctaaagta tatatgagta aacttggtct gacagttacc      5700
aatgcttaat cagtgaggca cctatctcag cgatctgtct atttcgttca tccatagttg      5760
cctgactccc cgtcgtgtag ataactacga tacgggaggg cttaccatct ggccccagtg      5820
ctgcaatgat accgcgagac ccacgctcac cggctccaga tttatcagca ataaaccagc      5880
cagccggaag ggccgagcgc agaagtggtc ctgcaacttt atccgcctcc atccagtcta      5940
ttaattgttg ccgggaagct agagtaagta gttcgccagt taatagtttg cgcaacgttg      6000
ttgccattgc tacaggcatc gtggtgtcac gctcgtcgtt tggtatggct tcattcagct      6060
ccggttccca acgatcaagg cgagttacat gatcccccat gttgtgcaaa aaagcggtta      6120
gctccttcgg tcctccgatc gttgtcagaa gtaagttggc cgcagtgtta tcactcatgg      6180
ttatggcagc actgcataat tctcttactg tcatgccatc cgtaagatgc ttttctgtga      6240
ctggtgagta ctcaaccaag tcattctgag aatagtgtat gcggcgaccg agttgctctt      6300
gcccggcgtc aatacgggat aataccgcgc cacatagcag aactttaaaa gtgctcatca      6360
ttggaaaacg ttcttcgggg cgaaaactct caaggatctt accgctgttg agatccagtt      6420
cgatgtaacc cactcgtgca cccaactgat cttcagcatc ttttactttc accagcgttt      6480
ctgggtgagc aaaaacagga aggcaaaatg ccgcaaaaaa gggaataagg gcgacacgga      6540
aatgttgaat actcatactc ttcctttttc aatattattg aagcatttat cagggttatt      6600
gtctcatgag cggatacata tttgaatgta tttagaaaaa taaacaaata ggggttccgc      6660
gcacatttcc ccgaaaagtg c                                                6681

<210> SEQ ID NO 12
<211> LENGTH: 6564
<212> TYPE: DNA
<213> ORGANISM: Artificial Sequence
<220> FEATURE:
<223> OTHER INFORMATION: Synthetic DNA Construct

<400> SEQUENCE: 12
cacctaaatt gtaagcgtta atattttgtt aaaattcgcg ttaaattttt gttaaatcag      60
```

```
ctcattttttt aaccaataggg ccgaaatcggg caaaatccct tataaatcaa aagaatagac      120 cgagatagggg ttgagtgttg ttccagtttg gaacaagagt ccactattaa agaacgtgga      180
ctccaacgtc aaagggcgaa aaaccgtcta tcagggcgat ggcccactac gtgaaccatc      240
accctaatca agttttttgg ggtcgaggtg ccgtaaagca ctaaatcgga accctaaagg      300
gagcccccga tttagagctt gacggggaaa gccggcgaac gtggcgagaa aggaagggaa      360
gaaagcgaaa ggagcgggcg ctagggcgct ggcaagtgta gcggtcacgc tgcgcgtaac      420
caccacaccc gccgcgctta atgcgccgct acagggcgcg tcccattcgc cattcaggct      480
gcgcaactgt tgggaagggc gatcggtgcg ggcctcttcg ctattacgcc agctggcgaa      540 aggggatgt gctgcaaggc gattaagttg ggtaacgcca gggttttccc agtcacgacg      600
ttgtaaaacg acggccagtg aattgtaata cgactcacta tagggcgaat tgggtaccgg      660
gccccccctc gaggtcgacg gtatcgataa gctaactaga atattaattg ctaaagtcaa      720
aaatctctaa tataagaaag aaaatattga aatgagaatt taatttaaaa ttaaatgata      780
atgcctatga gttaattaat ttgattaaag aaaggtattt gtttctttga gttcatattt      840
aatcaccagc acttaaaata tgttgatatt tgaattattt aaatactttc ttaaatatta      900
ttaccgtaat agtgtttgaa gtttaagaaa taatgtactt tggttataaa acaatttttt      960
tactattaat agaagggagt gactgtatat ttttcagccg aattattttt tttaaatatt     1020
cgaaattaaa aaataaaaag tttaaaatca taaaaattaa atgacatatc accacctgta     1080
cctacatagt tcgtgatatt ttaattacag gattagcaat atttatacat ataaaaatat     1140
taaatgcttt ttttaagatt ttagttattt ataaaatata cttataagat aaacaatttc     1200
aatttataat aatatattta aattcaatta aaatcctctt ttaaacttta ataattaaca     1260
aaacatttag cataatctgt tttgattgta gattttaaaa tagattaaat taaattatta     1320
agaaattttt tagaaaacta aaaaattaat ttacaaaaaa taaaatatta aacttacaaa     1380
ttaattaaaa tgaagaaatt tgttattta ataagcttga tatcgaattc agatcccccg     1440
ggctgcattt ttccagtaaa aatttgaaaa tttaatggca aaaaaaaata ttattattgg     1500
atttgcagac aaatttttaa gagctaacat gtatgtgaag aggaattttt ttttttagaa     1560
agttaaaaaa aataattgac ataaaatata tatacaaatg agttgtaaaa taatgatttt     1620
agtcaatttg gaataaatta tattttatag tagtatatta acacgttttt ttggtgcttt     1680
aatgttaata taatacacta aaaattaatt ttatataata tatttatttt atatgaaagt     1740
ttgtaaatat atattgaatt tttaatttaa ggatctcaga agaattcgtc aagaagacga     1800
tagaaggcga tacgttgaga atcgggagcg gcgataccgt aaaggacaag gaaacggtca     1860
gcccattcac caccaagttc ttcagcaata tcacgggtag ctaaggcaat atcttgataa     1920
cggtcggcga caccaagacg accacagtcg atgaaaccag aaaaacgacc attttcaacc     1980
atgatattgg gtaagcaggc atcaccatgg gtgacgacaa gatcttcacc gtcgggcata     2040
cgggccttaa gtctggcgaa aagttcggca ggggcaagac cttgatgttc ttcgtcaaga     2100
tcatcttgat cgacaagacc ggcttccata cgagtacgag cacgttcgat acgatgtttg     2160
gcttggtggt cgaaagggca ggtagcggga tcaagggtat gaagacgacg catagcatca     2220
gccatgatag aaactttttc ggcaggagca aggtgagaag aagaagatc ttgaccgggg     2280 acttcaccta aaagaagcca gtctctaccg gcttcagtga caacgtcaag gacagcagcg     2340
caaggaacac cggtggtggc aagccaagaa agacgggcag cttcatcttg aagttcatta     2400
```

```
agggcaccag aaaggtcggt cttgacgaaa agaacaggac gaccttgagc agaaagacgg    2460
aagacggcgg catcagagca accgatggtt tgttgagccc agtcataacc gaaaagtctt    2520
tcgacccaag cggcgggaga accagcgtgt aaaccatctt gttcaatcat tattttaagt    2580
ttagtattat tatttatttt attagagctt tattaaattt ttttaatttt tttaaattat    2640
ataaagaata aaaaagacga atatatatat atacactatt tacattattt tatatggatc    2700
attgtataaa tcgtgaatca cgtagctaag aattatatca gaaatataaa aaattacttt    2760
atattcaaga gagattcaag aatcacatct atattttaga atagaagaat tttgaaaatt    2820
agttaggttg actcatgatt taaatcatga gtcaatcaat ttatatttt tatcagaaat    2880 aaaaagattt acaaataatt catgacacaa aattcaagaa tcacaactta atattaaaat    2940
ataatagaaa cggataattg aaaataaaaa ataaatgata gcctaaataa tgagtaaatat   3000 tttgaaaatt aatgattcac atattataat tgatgaatga gctatgtttt gagcagctta    3060
tatatttaat aaataaaata attgatattt atctatttta tatttcatgt tttctttaaa    3120
aaacatgtca tcttttttat caatatattt gaaatttaaa gaaaataatt gaataaacga    3180
tacaatatat tttaagatat ataaaaaagt tttgctttca agatattaaa aatagtgata    3240
taaaaaataa gtactctatt atgttttttc ttattcagta ttatacctt aatcattatt    3300 atcttttat ttattttag ttagttattt tttatttta tgaatattta aagagctaaa    3360
aaaaatttaa aaatgtgtat ttaaattaaa ggagttattc aaaaccctta ttatttta    3420 tttttaaata ttttttagaa ataaattgta tatcgaattc ctgcagcaga cttcctctga    3480
tttcctaaca aagtaattct tacttttttg ttaaaacatt taaaaaaaaa caaaaatttt    3540
taataatttc taaaacgtgt tttatttaat ataaattcat gcatatggct aatatcttac    3600
gactttccta atatttaat tttataaatc tagattcaac ataaatagcg atcaactttt    3660
ttttatgagt cttaaaaatc tctacattta aaaacgaaaa attataagtt cagtcaactc    3720
caagctatta taagataatc atccatctaa aatcaataca gtcaattttt attttctata    3780
ttttcatagt ataaattttt atatttaaa ttgaaatttt tttaatttt cattttatta    3840 taaaaataga attagccaat ttgtaattta agatattaaa atttaatatt taaaattaaa    3900
tttacttaaa ggaaataaca taaaagtaaa acttacctta aaaattatga ttacctgtcc    3960
agaacatttt ttagcaatat aaaatatata tatccaaaat tttaaataaa attaaaaaaa    4020
actttgaata tattctgata taaaaatagt aaatacacaa tacatataaa aaaaaattca    4080
aatatttggt caaatttgat attatttaag ttcattatta attttaatta aataaataaa    4140
atatttacaa tcaatagtgt aaacttttaa atgataattt tacttttaga tataaatata    4200
aacaaacaaa atagagttat ataaaattta taaatagttt tagaaataat tcattttatt    4260
ttattttatt tgatgaaatt gtgttatgat aaaaaggaat ttacttattc ttcaattaga    4320
atacgctagc gcatgctcta gagcggccgc caccgcggtg gagctccagc ttttgttccc    4380
tttagtgagg gttaatttcg agcttggcgt aatcatggtc atagctgttt cctgtgtgaa    4440
attgttatcc gctcacaatt ccacacaaca tacgagccgg aagcataaag tgtaaagcct    4500
ggggtgccta atgagtgagc taactcacat taattgcgtt gcgctcactg cccgctttcc    4560
agtcgggaaa cctgtcgtgc cagctgcatt aatgaatcgg ccaacgcgcg gggagaggcg    4620
gtttgcgtat tgggcgctct tccgcttcct cgctcactga ctcgctgcgc tcggtcgttc    4680
ggctgcggcg agcggtatca gctcactcaa aggcggtaat acggttatcc acagaatcag    4740
gggataacgc aggaaagaac atgtgagcaa aaggccagca aaaggccagg aaccgtaaaa    4800
```

-continued

```
aggccgcgtt gctggcgttt ttccataggc tccgcccccc tgacgagcat cacaaaaatc   4860
gacgctcaag tcagaggtgg cgaaacccga caggactata aagataccag gcgtttcccc   4920
ctggaagctc cctcgtgcgc tctcctgttc cgaccctgcc gcttaccgga tacctgtccg   4980
cctttctccc ttcgggaagc gtggcgcttt ctcatagctc acgctgtagg tatctcagtt   5040
cggtgtaggt cgttcgctcc aagctgggct gtgtgcacga accccccgtt cagcccgacc   5100
gctgcgcctt atccggtaac tatcgtcttg agtccaaccc ggtaagacac gacttatcgc   5160
cactggcagc agccactggt aacaggatta gcagagcgag gtatgtaggc ggtgctacag   5220
agttcttgaa gtggtggcct aactacggct acactagaag gacagtattt ggtatctgcg   5280
ctctgctgaa gccagttacc ttcggaaaaa gagttggtag ctcttgatcc ggcaaacaaa   5340
ccaccgctgg tagcggtggt tttttgttt gcaagcagca gattacgcgc agaaaaaaag    5400
gatctcaaga agatcctttg atcttttcta cggggtctga cgctcagtgg aacgaaaact   5460
cacgttaagg gattttggtc atgagattat caaaaaggat cttcacctag atccttttaa   5520
attaaaaatg aagttttaaa tcaatctaaa gtatatatga gtaaacttgg tctgacagtt   5580
accaatgctt aatcagtgag gcacctatct cagcgatctg tctatttcgt tcatccatag   5640
ttgcctgact ccccgtcgtg tagataacta cgatacggga gggcttacca tctggcccca   5700
gtgctgcaat gataccgcga gacccacgct caccggctcc agatttatca gcaataaacc   5760
agccagccgg aagggccgag cgcagaagtg gtcctgcaac tttatccgcc tccatccagt   5820
ctattaattg ttgccgggaa gctagagtaa gtagttcgcc agttaatagt ttgcgcaacg   5880
ttgttgccat tgctacaggc atcgtggtgt cacgctcgtc gtttggtatg gcttcattca   5940
gctccggttc ccaacgatca aggcgagtta catgatcccc catgttgtgc aaaaaagcgg   6000
ttagctcctt cggtcctccg atcgttgtca gaagtaagtt ggccgcagtg ttatcactca   6060
tggttatggc agcactgcat aattctctta ctgtcatgcc atccgtaaga tgcttttctg   6120
tgactggtga gtactcaacc aagtcattct gagaatagtg tatgcggcga ccgagttgct   6180
cttgcccggc gtcaatacgg gataataccg cgccacatag cagaacttta aaagtgctca   6240
tcattggaaa acgttcttcg gggcgaaaac tctcaaggat cttaccgctg ttgagatcca   6300
gttcgatgta acccactcgt gcacccaact gatcttcagc atcttttact ttcaccagcg   6360
tttctgggtg agcaaaaaca ggaaggcaaa atgccgcaaa aaagggaata agggcgacac   6420
ggaaatgttg aatactcata ctcttccttt ttcaatatta ttgaagcatt tatcagggtt   6480
attgtctcat gagcggatac atatttgaat gtatttagaa aaataaacaa atagggggttc  6540 cgcgcacatt tccccgaaaa gtgc                                           6564
```

GENETICALLY ALTERED CILIATES AND USES THEREOF

CROSS-REFERENCE TO RELATED APPLICATIONS

This application claims priority to U.S. Provisional Patent Application Ser. No. 61/601,921, filed on Feb. 22, 2012, which is hereby incorporated by reference in its entirety.

The invention was made with government support under Grant No. GM077607 awarded by the National Institutes of Health. The government has certain rights in the invention.

BACKGROUND OF THE INVENTION

1. Field of the Invention

The present invention relates generally to the field of genetics and molecular biology. More particularly, it concerns genetically altered ciliate organisms and the use of such organisms in recombinant protein production.

2. Description of Related Art

Recombinant proteins are useful for a wide range of applications including as industrial enzymes and as therapeutics. For example, production of genetically engineered vaccine antigens, therapeutics (including antibodies and antibody fragments), industrial enzymes, biopolymers, and bioremediation agents now constitute a multibillion dollar-per-year industry. There is also a large market for recombinant proteins in the basic research arena (Pavlou and Reichert (2004); Langer (2005)).

Currently available platforms for the production of recombinant proteins are limited to a relatively small number of cell-based systems that include bacteria, fungi, and insect and mammalian tissue culture cells. Although bacteria can offer high yield and low cost alternatives for production of mammalian proteins, cell culture systems based on higher organisms such as insect cells or mammalian cell systems generally provide proteins having greater fidelity to the natural proteins in terms of protein folding and/or post-translational processing (e.g., glycosylation). Whole transgenic plants and animals have also been harnessed for the production of recombinant proteins, but the long development time from gene to final product can be a major drawback with these multicellular organisms, as can their high cost, low yield and many inherent difficulties in purification.

There remains a need in the art for improved methods for rapid, high-fidelity and cost-effective production and purification of recombinant polypeptides.

SUMMARY OF THE INVENTION

In a first embodiment a genetically altered ciliate is provided wherein the ciliate lacks detectable expression (or has reduced expression) of one or more SOR gene product. For example, the SOR gene product may be a product corresponding to SOR1 (SEQ ID NO: 1, 2), SOR2 (SEQ ID NO: 3, 4), SOR3 (SEQ ID NO: 5, 6) and/or SOR4 (SEQ ID NO: 7, 8; indicating the protein and nucleic acid coding sequence respectively). In some aspects, the ciliate may lack detectable expression of a SOR polypeptide or a SOR RNA corresponding to SOR1, SOR2, SOR3 and/or SOR4. In a further aspect, the ciliate lacks detectable expression of 2, 3 or 4 of the SOR1, SOR2, SOR3, or SOR4 genes. For example, a ciliate of the embodiments may lack detectable expression (or have reduced expression) of SOR1 and SOR2; SOR1 and SOR3; SOR1 and SOR4; SOR2 and SOR3; SOR2 and SOR4; SOR3 and SOR4; SOR1, SOR2 and SOR3; SOR1, SOR2 and SOR4; SOR1, SOR3 and SOR4; SOR2, SOR3 and SOR4; or SOR1, SOR2 SOR3 and SOR4.

In certain aspects, a ciliate of the embodiments comprises a genomic alteration, such as an insertion or a deletion in both copies of the germline genome that disrupts expression of one or more SOR gene product. For instance, the ciliate can comprise an insertion or deletion located in the open reading frame of a gene corresponding to SOR1, SOR2, SOR3 and/or SOR4. In some aspects, a genomic insertion comprises a selectable marker, such a drug resistance marker (e.g., a gene for tetracycline or neomycin resistance). Accordingly, in some aspects, a ciliate of the embodiments comprises an insertion or a deletion in all macronuclear copies of a gene corresponding to SOR1, SOR2, SOR3 and/or SOR4.

In further aspects a ciliate of the embodiments expresses a polynucleotide complementary to all or part of an RNA gene product corresponding to SOR1, SOR2, SOR3 and/or SOR4. For example, the ciliate can express an antisense RNA or a double stranded RNA (dsRNA) molecule, such as a small interfering RNA (siRNA), short hairpin RNA (shRNA) or micro RNA (miRNA), complementary to all or part of an RNA gene product corresponding to SOR1, SOR2, SOR3 and/or SOR4.

In still further aspects, a ciliate of the embodiments comprises a transgenic expression cassette, such as an expression cassette encoding a polypeptide. For example, the polypeptide can be a polypeptide for recombinant production in the ciliate. Polypeptides for use in accordance with the embodiments include, but are not limited to, enzymes, immunoglobulin (e.g., immunoglobulin light chains, immunoglobulin heavy chains or single chain antibodies), cytokines, chemokines, and antigens (e.g., bacterial or viral antigens). In some aspects the polypeptide coding sequence can comprise a sequence for cellular trafficking, such as a mucocyst-targeting sequence. For example, the polypeptide can encode a mucocyst-targeting sequence derived from a *Tetrahymena* Grl protein, such as Grl1, Grl2, Grl3, Grl4, Grl5, Grl6, Grl7, Grl8, Grl9 or Grl 10. In still further aspects, the polypeptide encodes a cleavable linker (e.g., between the polypeptide for expression and a mucocyst-targeting sequence).

In some specific aspects, a ciliate of the embodiments is a *Tetrahymena*, such as a *T. thermophila* or *T. pyriformis*.

In yet a further embodiment there is provided a recombinant *Tetrahymena* germline genome (e.g., a recombinant *T. thermophila* or *T. pyriformis* genome) comprising a genomic insertion or deletion in both copies of one or more SOR gene selected from the group consisting of SOR1, SOR2, SOR3, and SOR4. For example, the genomic insertion or deletion can be located in the open reading frame of the gene. In some aspects, a genomic insertion comprises the insertion of a selectable marker, such a drug resistance marker. In still further aspects, a *Tetrahymena* germline genome comprises a genomic insertion or deletion in both copies of 2, 3 or 4 SOR genes corresponding to SOR1, SOR2, SOR3 or SOR4. Thus, the genome can comprise an insertion of deletion in the genes for SOR1 and SOR2; SOR1 and SOR3; SOR1 and SOR4; SOR2 and SOR3; SOR2 and SOR4; SOR3 and SOR4; SOR1, SOR2 and SOR3; SOR1, SOR2 and SOR4; SOR1, SOR3 and SOR4; SOR2, SOR3 and SOR4; or SOR1, SOR2 SOR3 and SOR4.

In a further embodiment there is provided a recombinant *Tetrahymena* germline genome comprising, an expression cassette comprising a sequence encoding a polynucleotide molecule complementary to all or part of an RNA gene product corresponding to SOR1, SOR2, SOR3, or SOR4. For example, genome can comprise sequences encoding an antisense RNA or a dsRNA, such as a siRNA, shRNA or miRNA, complementary to all or part of an RNA gene product corresponding to SOR1, SOR2, SOR3 and/or SOR4.

In still a further aspect of the embodiments a recombinant *Tetrahymena* germline genome can comprise a transgenic expression cassette, such as a cassette encoding a polypeptide, optionally including a mucocyst-targeting sequence.

In still yet a further embodiment there is provided a method of producing a genetically altered ciliate comprising: (a) transforming a ciliate with a polynucleotide comprising a sequence complementary to a SOR gene corresponding to SOR1, SOR2, SOR3 and/or SOR4; and (b) isolating a genetically altered ciliate wherein the ciliate lacks detectable expression of the gene product of said SOR gene. For example, step (b) can comprise isolating a genetically altered ciliate comprising an insertion or deletion in a SOR gene or isolating a genetically altered ciliate expressing a polynucleotide molecule complementary to all or part of an RNA gene product of a SOR gene. In further aspects, step (a) comprises transforming the ciliate with a polynucleotide comprising a sequence complementary to a SOR gene and comprising a selectable marker (e.g., a drug resistance marker). Thus, in some aspects, a genetically altered ciliate is isolated based on expression of a selectable marker (such as by drug selection). Detailed methods for genetic alteration of ciliates are well known in the art and are detailed in PCT Patent Publn. No. WO2010108182, the entirety of which is incorporated herein by reference.

In a further embodiment there is provided a method of producing a genetically altered ciliate of the embodiments comprising obtaining the genetically altered ciliate and vegetatively propagating the ciliate. In further aspects, a genetically altered ciliate can be a produced by sexually propagating a genetically altered ciliate and isolating progeny that comprise the genetic alterations.

In still yet a further embodiment a method of producing a polypeptide is provided comprising: (a) expressing a polynucleotide encoding the polypeptide in a ciliate of the embodiments; and (b) incubating the ciliate in a media under conditions permissible for expression of the polypeptide. In some aspects, the majority (or at least a portion) of the polypeptide is secreted from the ciliate and the method can comprise (c) purifying the expressed polypeptide from the media. In certain aspects, the majority (or at least a portion) of the polypeptide is not secreted by the ciliate and the method can comprise (c) purifying the ciliate from the media and, optionally, (d) purifying the protein from the ciliate. In still further aspects, a method of the embodiments further comprises transforming a ciliate with a polynucleotide encoding a polypeptide. Further methods for polypeptide expression in ciliates are detailed in PCT Patent Publn. No. WO2010108182, the entirety of which is incorporated herein by reference.

In some aspects a expressing a polynucleotide for expression in a ciliate is further defined as an expression cassette encoding a polypeptide. For example, the polypeptide can be a polypeptide of mammalian origin, such as a human polypeptide. In some aspects, the polypeptide comprises sequence encoding an enzyme, an immunoglobulin, a cytokine, a chemokine, or an antigen.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Two sortilin genes in *Tetrahymena* are dramatically up-regulated during induced granule formation (regranulation) in *Tetrahymena*. First column show fold induction of the genes, significance values are shown in third column.

DESCRIPTION OF ILLUSTRATIVE EMBODIMENTS

Recombinant protein production has become very important for a variety of applications. For example, many modern therapeutics, such as enzymes and monoclonal antibodies, are proteins that are produced recombinantly. However, adequate and cost-effective protein production systems are lacking Bacterial expression systems, while low cost, often result in proteins that do not incorporate crucial post-translation modifications or are improperly folded. On the other hand, mammalian cell expression systems are very expensive to maintain and produce notoriously low yields of protein products that must be extensively purified. Accordingly, ciliate-based protein production systems could provide an attractive alternative existing systems. However, there remains a need for a ciliate system adapted to provide high quality recombinant protein yield.

Figure 3:
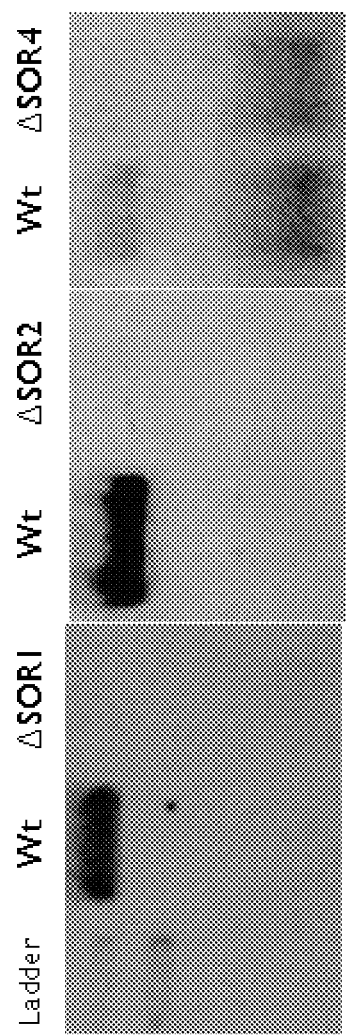
FIG. 3: *Tetrahymena* RNA expression was examined in putative SOR knockout lines (SORT, SOR2 and SOR4). In each case wild type (WT) *Tetrahymena* exhibited SOR RNA expression, whereas no expression was observed in the knockout lines.
Figure 4:
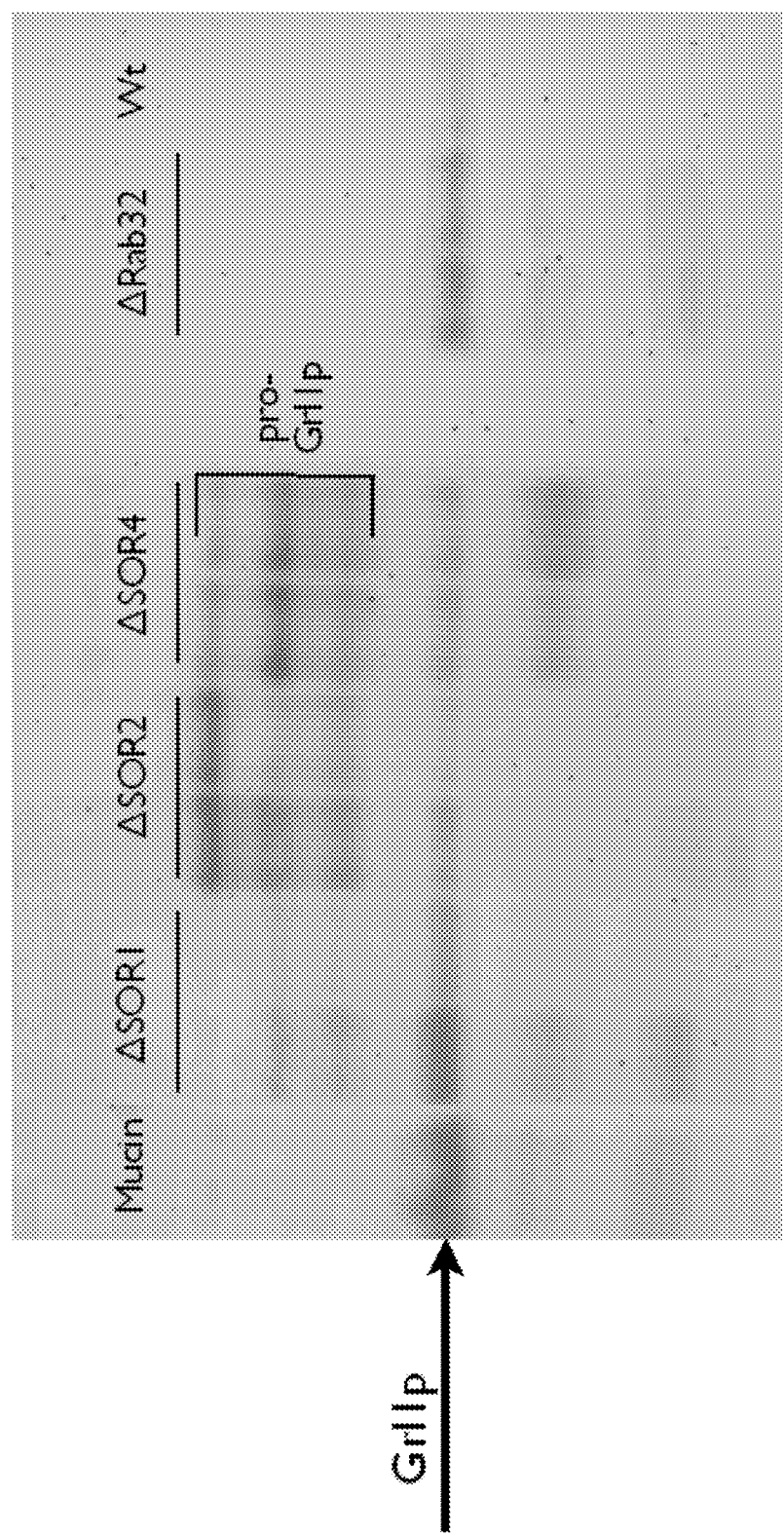
FIG. 4: *Tetrahymena* sortilin knockout lines secrete unprocessed precursors of the granule protein Grl1p. Immunoblot media samples show that in the case of each of the SOR knockout lines unprocessed (high molecular mass) Grl1p precursors are released into the media.
Figure 5:
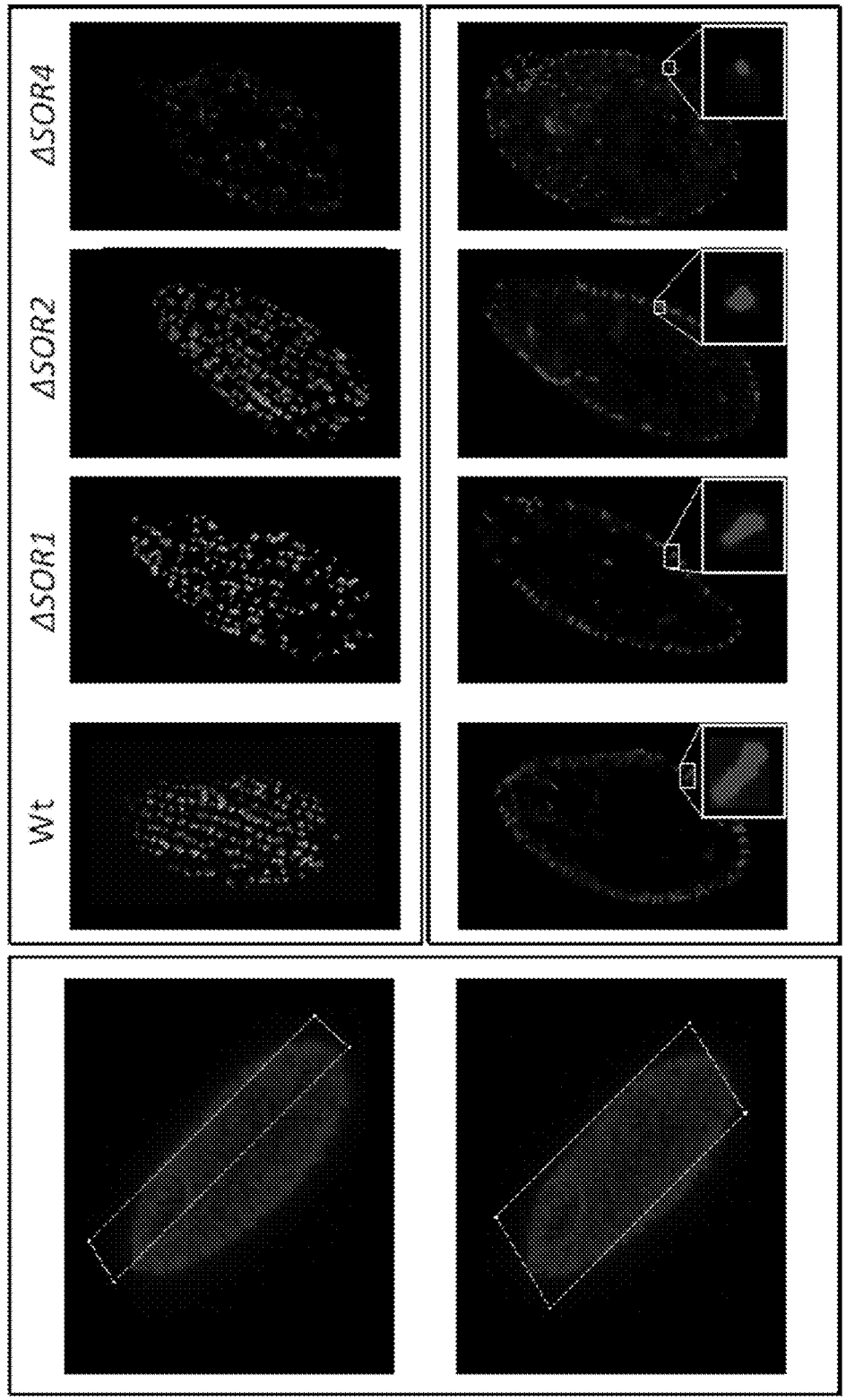
FIG. 5: The sortilin knockout lines each make aberrant secretory granules, which are visualized here by immunefluorescence. Granule-specific immunefluorescence results for the indicated knockout cells (or for wild type "wt") are shown in tangential section (upper panels) or equatorial section (lower panels).

Studies detailed herein identify four ciliate gens from *Tetrahymena* that are important regulators of cell trafficking and secretion pathways. In particular, the SOR genes mediate transport of proteases to granules allowing for proteolytic processing of the granule contents. The studies here demonstrate that SOR gene expression can effectively knocked-out (see, FIG. 3), and that such knockout is not lethal to the organism. Indeed, knockout of SORT, SOR2 and SOR4 all resulted in decreased proteolytic processing of products located in granules (FIG. 4) and a change in granule structure indicative of reduced proteolytic processing (FIG. 5).

Accordingly, modified ciliate organisms, such as *Tetrahymena*, are provided that have reduced expression of one or more sortilin gene product. Importantly, these organism exhibit reduced proteolytic processing in granules and are thereby ideal for recombinant protein production. Such organisms can be used to produce a wide range of protein products without aberrant cleavage of the products during expression. Moreover, recombinant proteins can be easily and cost-effectively purified by either isolating the ciliate cells comprising large quantities of highly concentrated (and uncleaved) protein product or by targeting the proteins for secretion and isolating the product from cell media.

I. Ciliates for Use According to the Embodiments

The embodiments may be practiced with a variety of different ciliates which include secretory granules called mucocysts. Heterologous polypeptides can be targeted to these secretory granules by encoding fusion proteins of the desired heterologous polypeptide and an appropriate targeting sequence. After exposing the ciliate to a secretory stimulus that causes the mucocysts to discharge their contents to the extracellular environment, the heterologous polypeptide can be recovered from the resulting matrix and medium.

The free-living ciliate protists are a large and diverse phylum (Ciliata) whose members display a structural and functional complexity comparable to that of higher metazoa (Fankel (2000); Turkewitz et al. (2002)), and include over 7,000 species with 11 major subdivisions. Tetrahymenids and Paramecium belong to the Oligohymenophoreans. Ciliates that include mucocysts useful in the invention include *Tetrahymena* species such as *Tetrahymena thermophila* and *Tetrahymena pyriformis*. Paramecium has dense core granules but does not secrete a proteinaceous gel. Both *Tetrahymena thermophila* and *Tetrahymena pyriformis* produce mucocysts, and both secrete a proteinaceous gel.

*Tetrahymena* spp. are amenable to genetic manipulation, can be grown on a large scale and have a doubling time of 1.5-3 hrs. Unlike *T. thermophila*, which has an optimal growth temperature of 35° C., the optimal growth temperature for *T. pyriformis* is lower (maximal growth temperature of 34° C.). Cells reach high-density in a short time on a variety of inexpensive media and can be expanded for growth in bioreactors up to several thousand liters in size (Hellenbroich et al. (1999); de Coninck et al. (2000)). Methods for transformation, along with robust, inducible promoters for driving high-level gene expression have recently been described for this system (Bruns and Cassidy-Hanley (2000); Gaertig and Kapler (2000); Shang et al. (2002); Boldrin et al. (2006)).

*Tetrahymena* spp. devote a large part of their metabolism to membrane protein production due to the hundreds of cilia that extend from its surface (Williams et al. (1980)). Additionally, *Tetrahymena* spp. lack a cell wall and display high-mannose N-glycan protein modifications that lack branched, immunogenic structures (Taniguchi et al. (1985); Becker and Rusing (2003); Weide et al. (2006)). Glycosylation patterns of secreted proteins in *Tetrahymena* spp. are uniform and consist of high-mannose N-glycan structures comprising Man3GlycNac2 core N-glycans similar to those which are produced in the endoplasmic reticulum of mammalian cells.

This glycosylation pattern is unlike the glycosylation pattern produced in other microbial systems. For example, such glycosylation is non-existent in bacteria, and is highly branched and immunogenic in fungi.

II. Genetic Alteration of Ciliates

Methods for genetic alteration of ciliates are well known in the art and may be used in accordance with the instant embodiments. For example, ciliates can be transformed with vectors that express nucleic acid to disrupt expression of a SOR gene (such as siRNAs). In some aspects, the ciliates is transformed with a vector to disrupt an endogenous SOR gene (e.g., by generating an insertion of deletion in a genomic copy of the gene). In still further aspects, a ciliate can be transformed with a vector for the expression of heterologous polypeptides, such as peptides that will be harvested from the cells.

Certain aspects of the embodiments concern ciliates that lack detectable expression (or have reduced expression) of one or more SOR gene product corresponding to SOR1, SOR2, SOR3 or SOR4. In some aspects the SOR gene product is an RNA at least about 75%, 80%, 85%, 90%, 91%, 92%, 93%, 94%, 95%, 96%, 97%, 98% or 99% identical to the nucleic acid sequence of SOR1 (SEQ ID NO: 2), SOR2 (SEQ ID NO: 4), SOR3 (SEQ ID NO: 6) or SOR4 (SEQ ID NO: 8). In a further aspect, the SOR gene product is an polypeptide at least about 75%, 80%, 85%, 90%, 91%, 92%, 93%, 94%, 95%, 96%, 97%, 98% or 99% identical to the amino acid sequence of SOR1 (SEQ ID NO: 1), SOR2 (SEQ ID NO: 3), SOR3 (SEQ ID NO: 5) or SOR4 (SEQ ID NO: 7). In yet further aspects the SOR gene product is an polypeptide comprising at least 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890 or 900, contiguous amino acids identical to the amino acid sequence of SOR1 (SEQ ID NO: 1), SOR2 (SEQ ID NO: 3), SOR3 (SEQ ID NO: 5) or SOR4 (SEQ ID NO: 7). In some specific aspects, the gene product corresponding to SOR1, SOR2, SOR3 or SOR4 is one of the gene products listed in the NCBI accession numbers of FIG. 2, each of which is incorporated herein by reference. Thus, in some aspects, a ciliate of the embodiments comprises an insertion or a deletion in such a gene corresponding to *Tetrahymena* SOR1, SOR2, SOR3 and/or SOR4. In yet further aspects, a ciliate can comprise an expression cassette encoding a polynucleotide (e.g., a dsRNA, siRNA, shRNA or miRNA) complementary to all or part of an RNA corresponding to a *Tetrahymena* SORT, SOR2, SOR3 and/or SOR4 RNA.

Transformation

Genes can be introduced into ciliates using established protocols or any method known to one skilled in the art. Transformation of ciliates can be achieved by microinjection (Tondravi and Yao (1986)), electroporation (Gaertig and Gorovsky (1992)), or biolistically (Cassidy-Hanley et al. (1997)).

Thus, in some embodiments, ciliate cells can be transformed with a chimeric gene by particle bombardment (also known as biolistic transformation) (Cassidy-Hanley et al. (1997)). Particle bombardment transformation can be achieved by several ways. For example, inert or biologically active particles can be propelled at cells under conditions effective to penetrate the outer surface of the cell and to be incorporated within the interior thereof. When inert particles are utilized, the vector can be introduced into the cell by coating the particles with the vector containing the chimeric gene. Alternatively, the target cell can be surrounded by the vector so that the vector is carried into the cell by the wake of the particle. Other variations of particle bombardment, now known or hereafter developed, can also be used.

Microcarrier bombardment can also be used to transform ciliate cells by means of DNA-loaded gold particles (U.S. Pat. No. 6,087,124; European Pat. EP 847 444; WO 1998/001572). In this approach, microcarrier bombardment with DNA-coated gold is used as a means of introducing foreign genes into ciliates. In one embodiment, microcarrier bombardment can be used to transform ciliates and introduce genes into the (germline) micronucleus Methods for selection of transformed cells harboring foreign genes are known in the art. For example, the vector can further comprise a selectable cassette marker to permit selection for transformed cells {e.g., a neo 2 cassette) (Gaertig et al. (1994)).

Selection of transformants can be achieved by growing the cultured ciliates in a medium which allows only the transformants to survive. Suitable selection agents include antibiotics which will kill most all non-transformants but allow transformants (which also possess an antibiotic resistance gene) to survive. A number of antibiotic-resistance markers are known in the art. Any known antibiotic-resistance marker can be used to transform and select transformed host cells in accordance with the present invention. For example, selection of the transformants can be performed by means of a resistance marker such as a point mutation in the 17s rDNA, which confers resistance to paromomycin, can allow for selection of rDNA transformants (Spangler and Blackburn (1985); Bruns et al. (1985)). Other methods include the use of a mutant cell line that allows targeting of genes to the beta tubulin-1 locus of T. thermophila by homologous recombination, and allows efficient selection of transformed cell lines by growth in the microtubule-stabilizing agent (taxol) (U.S. Pat. No. 6,846,481). Another method for selection of transformed cells harboring foreign genes is to insert full length coding regions into the pD5HA vector (Cowan et al. (2005)). In this method, transcription is driven by the inducible MTT1 promoter. Once cells have been transformed with the pD5HA vector selection of positive transformants is determined by paromomycin resistance (i.e., cell growth in media containing the drug). Presence of the transgene is then verified by PCR and then induced with cadmium chloride to over-express the recombinant gene product.

Many other selectable marker systems are known in the art. Selectable marker genes that confer resistance or tolerance to a normally toxic selection agent allow only successfully transfected cells to survive in the presence of the selection agent, and are referred to as positive selectable markers. Examples of positive selectable marker genes and their corresponding selection agents are: aminoglycoside phosphotransferase (APH) and G418; dihydro folate reductase (DHFR) and methotrexate (Mtx); hygromycin-B-phosphotransferase (HPH) and hygromycin-B; xanthine-guanine phosphoribosyltransferase (XGPRT) and mycophenolic acid; and adenosine deaminase (ADA) and 9-β-D-xylofuranosyl adenine (XyI-A). In another example of a positive selectable marker system, thymidine kinase (TK) and aminopterin (included, e.g., in hypoxanthine-aminopterin-thymidine (HAT) medium) can be used in cells that are initially thymidine kinase deficient (tk~). The aminopterin will normally kill tk~ cells and, therefore, only successful TK transfectants will survive. Selectable marker genes that confer sensitivity or susceptibility to a normally nontoxic selection agent cause only successfully transfected cells to die in the presence of the selection agent, and are referred to as negative selectable markers. An example of a negative selectable marker system is thymidine kinase (TK) and gancyclovir. Phenotypic selectable marker genes permit selection based upon morphological or biochemical traits rather than cell death or survival. In some cases, the phenotypic marker is detectable only in the presence of an additional selection agent. An example of a phenotypic selectable marker system is β-galactosidase (lacZ) and X-gal.

III. Vectors and Polypeptide Expression

Heterologous nucleic acids can be introduced into the ciliate host on an expression vector that is capable of integrating into the host's genome. For example, expression vectors capable of homologous recombination with a highly expressed gene that is endogenous to the protozoan host, such as a P-tubulin gene are known in the art. Alternatively, a heterologous nucleic acid transformed into a ciliate can be maintained extrachromosomally on an autonomous plasmid.

Expression vectors useful for transforming ciliates in accordance with the methods described herein include but are not limited to replacement vectors, rDNA vectors, and rDNA-based vectors. Replacement vectors accomplish DNA-mediated transformation by replacing or altering endogenous genes using homologous recombination. Integration of the heterologous nucleic acid into the host's genome at the targeted site is accomplished via homologous recombination involving a double crossover event with the vector containing the heterologous nucleic acid. An example of an expression vector useful for genomic incorporation of a heterologous nucleic acid by replacement is one that includes a heterologous coding sequence flanked by portions of the endogenous BTU1 gene of Tetrahymena thermophile.

A replacement vector can include a 5' region, followed by a heterologous coding region, followed by a 3' region, wherein at least a portion of each of the 5' and 3' regions is complementary to 5' and 3' regions on an endogenous gene of the host, to allow for genomic integration of the heterologous coding region via homologous recombination. The 5' and 3' regions of the vector can also comprise regulatory elements, such as a promoter and a terminator. The necessary regulatory elements can also be supplied by the endogenous gene into which the heterologous coding region integrates. Suitable regulatory regions include, but are not limited to promoters, termination sequences, signal peptides and proprotein domains involved in the expression and secretion of proteins. For example, such regulatory elements can provide efficient heterologous expression of proteins in Tetrahymena spp. under control of promoters and/or terminators which are derived from genes in Tetrahymena ssp. Such vectors can comprise naturally occurring promoters and/or terminators from proteins secreted at a high level in Tetrahymena ssp. The expression of recombinant polypeptides in Tetrahymena spp. can be driven by strong promoters, pre/pro sequences and terminators. In one embodiment, the promoters and/or terminators can be selected from proteins secreted at a high level independent of the cell-cycle in Tetrahymena spp. (US Patent Application 2006/0127973; WO2003/078566). Inducible promoters from Tetrahymena spp. genes have also been described that allow robust expression of foreign genes. For example, heat-inducible promoters of the heat shock protein family of the ciliate Tetrahymena spp. are also suitable for use with the methods described herein. Suitable heat shock promoters from *Tetrahymena* spp. are known in the art (see WO2007/006812).

Methods for creating mitotically stable *Tetrahymena* spp. transformants, for example, by integration of a heterologous gene by homologous DNA recombination, are known in the art. Methods for generating *Tetrahymena* spp. having targeted gene knockouts by homologous DNA recombination are also known in the art (Bruns and Cassidy-Hanley (2000); Hai et al. (2000); Gaertig et al. (1999); Cassidy-Hanley et al. (1997)). The somatic macronucleus or the generative micronucleus can be transformed in alternation. For example, sterile transformants, which may provide improved safety parameters, can be obtained with macronucleus transformation.

Expression vectors can also be maintained extrachromosomally in the ciliates. An expression vector maintained as an extrachromosomal element can be a rDNA-based vector containing an on from *Tetrahymena* spp. rDNA, which is known to support extrachromosomal replication. Such a vector can further comprise a 5' regulatory region from an endogenous *Tetrahymena* spp. gene containing a promoter region operably linked to the heterologous coding region and, optionally, a 3' regulatory region from the same or a different *Tetrahymena* spp. gene. For example, regulatory regions from ciliate genes in such vectors can include, but are not limited to, regulatory regions from genes such as HHFI, rp129, BTU1, BTU2, SerH3, and actin.

There are a number of suitable vectors suitable for transformation of ciliates known in the art. For example, *Tetrahymena* spp. can be transformed with an rDNA vector (Tondravi and Yao (1986); Yu and Blackburn (1989)). The shuttle vector pXS76 allows insertion of transgenes downstream of a cadmium-inducible promoter from the MTT1 metallothionein gene of *T. thermophila* via homologous recombination and selection in paromomycin. Alternatively, inserts can be introduced into high copy number ribosomal DNA vectors (such as pD5H8) under control of the cadmium-inducible MTT1 promoter. The pD5H8 vector takes advantage of a biological feature of *Tetrahymena* spp. in which the ribosomal cistrons become amplified to extraordinarily high copy numbers following conjugation. An rDNA-based vector can be a circular vector that contains a 5' non-translated sequence comprising two or more on sequences from *Tetrahymena* spp. rDNA. A nucleic acid fragment containing a heterologous coding region, for example a selectable marker or transgene, can also be added to the vector. The vector can further comprise a 5' untranslated region of a *Tetrahymena* spp. gene and a 3' untranslated region of a *Tetrahymena* spp. gene, inserted upstream and downstream of the selectable marker and/or the transgene. Methods for transformation, along with robust, inducible promoters for driving high-level gene expression have recently been described for this system (Bruns and Cassidy-Hanley (2000); Gaertig and Kapler (2000); Shang et al. (2002); Boldrin et al. (2006)).

Sequence variations within the origins of replication of rDNA from wild-type B- and C3-strains of *T. thermophila* convey a replicative advantage to the C3-form in B/C3 heterozygotes. Although both B- and C3-forms of rDNA are initially present in the macronucleus in approximately equal amounts, within 30 fissions only the C3 variant remains (Pan et al. (1982); Orias et al. (1988)). pIC19-based shuttle vectors containing the C3 origin of replication have been used as high-copy number vectors for the delivery of foreign DNA to *Tetrahymena* spp. (Yu and Blackburn (1989)) (FIG. 5).

Although such vectors can become unstable and be lost within about 50 to about 80 generations, micronuclear versions of the C3 rDNA is accurately processed (to form a palindrome) following introduction into *T. thermophila* B cell lines. The micronuclear version is maintained as a stable linear chromosome over many generations (Bruns et al. (1985)). Functional transgenes can be inserted into the 3'-nontranscribed spacer (3'-NTS) of such vectors with no effect on rDNA processing. Within 6-10 generations, recombinant molecules can comprise 50-100% of the total rDNA complement, with as many as 18,000 copies of the transgene per cell (Blomberg et al. (1997)). The use of this approach enables an increase in the number of cloned genes in transformed cell lines by orders of magnitude and leads to increased expression at the protein level. For example, the use of rDNA-based vectors in combination with the MTT1 promoter can be used to drive expression of the endogenous granule lattice protein GrI Ip to approximately 20% of total cell protein (Lin et al. (2002)). Similarly, pD5H8 rDNA-based vectors (Blomberg et al. (1997)) can be used to boost expression of proteins by at least 3-10 fold compared with trans formants in which respective transgenes are integrated at somatic gene loci. Other vectors suitable for use with the methods described here include vectors comprising a ribosomal DNA sequence. Such vectors can replicate at high copy numbers and can be used to deliver a heterologous DNA sequence to *Tetrahymena* spp. for purposes of RNA expression.

Heterologous Polypeptides

Suitable heterologous polypeptides for use with these methods include, but are not limited to, antibodies, antibody fragments, cytokines, growth factors, protein kinases, proteases, protein hormones or any fragment thereof. Similarly, the methods described herein are suitable for the production of specialty proteins. The use of such specialty proteins can include, but is not limited to, prototype vaccines for animal model studies, structural studies, or as therapeutic proteins. For example, quantities of antigens can be produced according to the methods described herein.

Isolation of Desired Polypeptides from the Mucocyst Matrix

In one aspect, the invention provides methods for protein purification from the extracellular matrix formed by the discharge of mucocysts. Because heterologous polypeptides targeted to the mucocyst compartment will be associated within the matrix, the invention provides matrix-based purification strategies. Advantageously, the matrix can be used for rapid purification of recombinant polypeptides associated with it.

Proteins within the gel matrix can be separated from cellular constituents by low-speed centrifugation (See Turkewitz et al. (2000)). Any other method known in the art suitable for separating intact cells, from the discharged material, including, but not limited to filtration harvesting using an appropriately selected mesh, can also be used in conjunction with the methods described herein. After isolation of the matrix, the desired heterologous polypeptide can be liberated from the secreted matrix gel. Methods for liberation of the protein can include chemical methods {e.g., high salt concentrations) and/or enzymatic methods {e.g., site-specific proteases).

Proteins can also be isolated in intact secretory granules. For example, the use of an exocytosis-defective mutant, MN 173, of *T. thermophile* where granules accumulate in the cytoplasm has been described for such purposes (Melia et al. (1998)).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Sortilin Gene Control Granule Trafficking of Proteases in *Tetrahymena*

Figure 2:
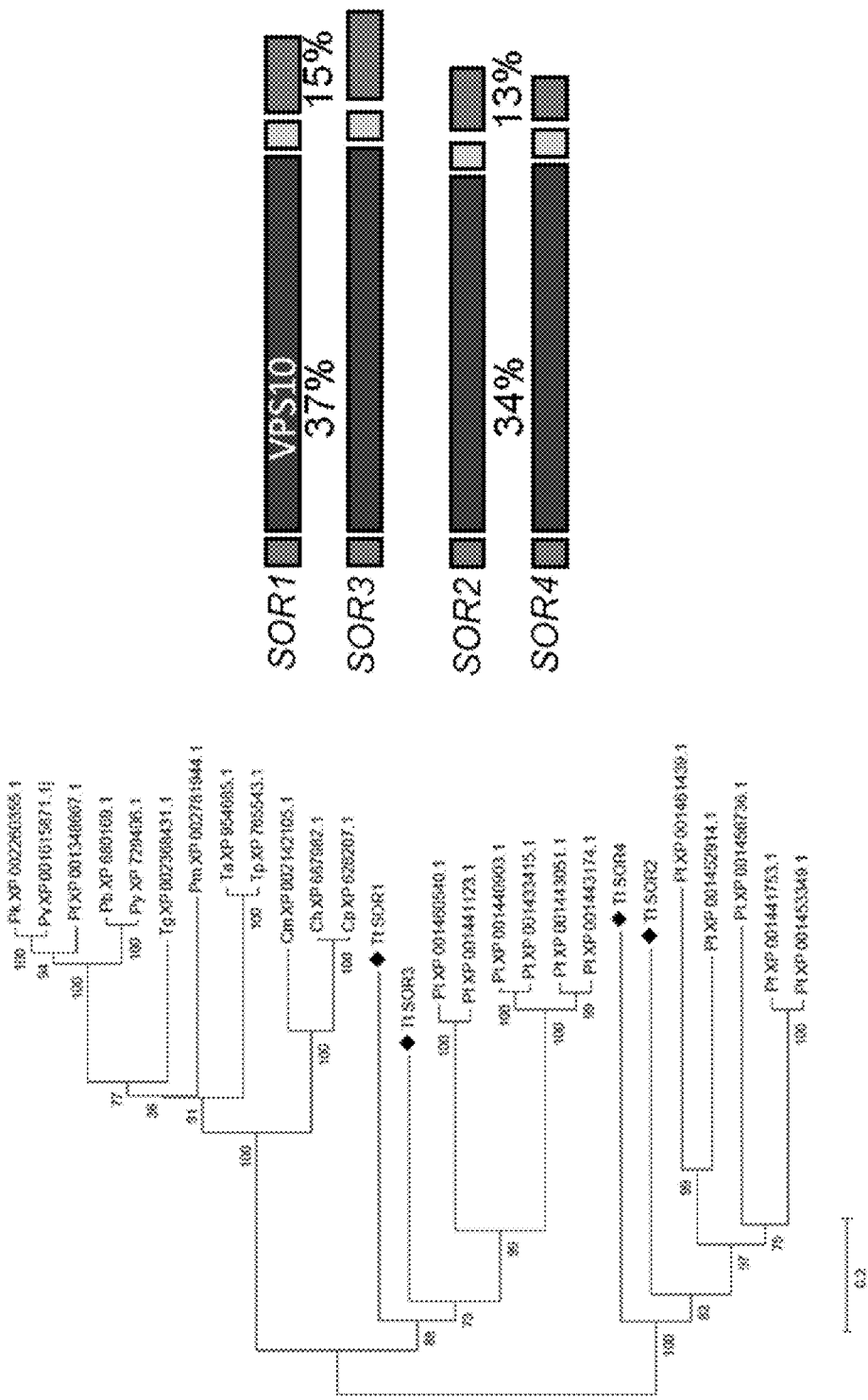
FIG. 2: Analysis of the *Tetrahymena* genome indicates that it codes four sortilin/Vps10 genes. Diagram shows the homology between the four sortilin genes (Tt SOR1-4) and structurally related genes.

Initial studies were undertaken to identify genes that are up-regulated upon regranulation in *Tetrahymena* cells. Results shown in FIG. 1 demonstrate that two sortilin genes are among the genes that are dramatically up-regulated during this process. In view of these studies, the *Tetrahymena* genome was analyzed in comparison with genes from other organisms and four *Tetrahymena* sortilin genes were identified (FIG. 2). The identified genes were SOR1, SOR2, SOR3, and SOR4, corresponding to NCBI accession nos. XM_001033316.2, XM_001020814.3, XM_001025035.2 and XM_001033494.2, each incorporated herein by reference.

To further determine the function of the SOR genes vectors were constructed to knockout each of the genes *Tetrahymena* (by homologous recombination targeting to the SOR ORFs). The vectors used in the studies are provided as SEQ ID NOs: 9-12, for targeting SOR1, SOR2, SOR3 and SOR4 respectively. Following transformation, knockout cells were successfully isolated for SOR1, SOR2 and SOR4. Studies shown in FIG. 3 confirm that in each case the knockout lines lack detectable expression of the indicated sortilin RNA. Moreover, knockout of the sortilin genes hampered proteolytic processing in the knockout cells. As shown in FIG. 5, unprocessed forms of Grl1p (pro-Grl1p) were observed in the media of the knockout lines, but not in that of wild type cells or a knockout of the Rab32 gene. Thus the sortilin knockouts result in an inability to effect the normal proteolytic processing of granule proteins.

Immunofluorescence studies were also performed to visualize granules in knockout and wild type cells. Results, shown in FIG. 5, demonstrate that wild type granules are elongated, a shape that is generated by the proteolytic processing of the content proteins. The granules in the sortilin knockout lines are spherical, consistent with the failure to proteolytically process the contents.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 6,846,481
U.S. Pat. No. 6,087,124
U.S. Patent Appln. 2006/0127973
Becker and Rusing, *J. Eukaryot. Microbiol.*, 50:235-239, 2003.
Blomberg et al., *Mol. Cell. Biol.*, 12:7237-747, 1997.
Boldrin et al., *Eukaryot Cell*, 2:422-425, 2006.
Bruns and Cassidy-Hanley, *Meth. Cell Biol.*, 62:501-512, 2000.
Bruns et al., *Proc. Natl. Acad. Sci. USA*, 9:2844-286, 1985.
Cassidy-Hanley et al. *Genetics*, 146:135-147, 1997.
Cowan et al., *Mol. Cell. Biol.*, 16:4046-4060, 2005.
de Coninck et al., *J. Industr. Microbiol. Biotechnol.*, 24:285, 2000.
European Patent EP 847 444
Fankel, *Meth. Cell Biol.*, 62:27-125, 2000.
Gaertig and Gorovsky *Proc. Natl. Acad. Sci. USA*, 89:9196-9200, 1992.
Gaertig and Kapler, *Meth. Cell Biol.*, 62:486-500, 2000.
Gaertig et al. *Nucleic Acids Res.*, 22:5391-5398, 1994.
Gaertig et al., *Nature Biotech.*, 17:462-465, 1999.
Hai et al., *Meth. Cell Biol.*, 62:513-531, 2000.
Hellenbroich et al. *Appl. Microbiol. Biotechnol.*, 51:447, 1999.
Langer, $3^{rd}$ Annual Rept and Surv. Biopharm. Manufact. Capacity and Prod., BioPlan Assoc., Inc. (2005
Lin et al. *Gene*, 288(1-2):85-94, 2002.
Melia et al., *J. Cell Sd. H*, 1(Pt 1):131-140, 1998.
Orias et al., *Gene*, 2:295-301, 1988.
Pan et al., *Cell*, 3:595-604, 1982.
Pavlou and Reichert, *Nat. Biotechnol.*, 22:1513-1519, 2004.
PCT Publn. WO 1998/001572
PCT Publn. WO 2003/078566
PCT Publn. WO 2007/006812
PCT Publn. WO 2010/108182
Shang et al., *Proc. Natl. Acad. Sci. USA*, 6:3734-379, 2002.
Spangler and Blackburn, *J. Biol. Chem.*, 10:6334-6340, 1985.
Taniguchi et al., *J. Biol. Chem.*, 260:13941-13946, 1985.
Tondravi and Yao, *Proc. Natl. Acad. Sci. USA*, 83:4369-4373, 1986.
Turkewitz et al., *Meth. Cell Biol.*, GI-MI-IGI, 2000.
Weide et al., *BMC Biotechnol.*, 6:19, 2006.
Williams et al., *J. Biol. Chem.*, 255:296-303, 1980.
Yu and Blackburn, *Proc. Natl. Acad. Sci. USA*, 21:8487, 891, 1989.

What is claimed is:

1. A genetically altered ciliate wherein the ciliate lacks detectable expression of one or more sortilin (SOR) gene products selected from the group consisting of SOR1, SOR2, SOR3, and SOR4.

2. The ciliate of claim 1, wherein the one or more sortilin (SOR) gene products has a sequence selected from the group consisting of SEQ ID NO: 1, SEQ ID NO: 3, SEQ ID NO: 5, and SEQ ID NO: 7.

3. The ciliate of claim 1, wherein the ciliate comprises a genomic alteration of one or more of SOR1, SOR2, SOR3, or SOR4.

4. The ciliate of claim 3, wherein the ciliate comprises a deletion in both copies of the ciliate's germline genome that disrupts expression of a SOR gene product.

5. The ciliate of claim 3, wherein the ciliate comprises an insertion in both copies of ciliate's germline genome that disrupts expression of a SOR gene product.

6. The ciliate of claim 5, wherein the insertion is located in the open reading frame of one or more SOR genes selected from the group consisting of SOR1, SOR2, SOR3, and SOR4.

7. The ciliate of claim 1, wherein the ciliate lacks detectable expression of 2, 3, or 4 gene products selected from the group consisting of SOR1, SOR2, SOR3, and SOR4.

8. The ciliate of claim 1, wherein the ciliate expresses a polynucleotide complementary to all or part of an RNA gene product selected from the group consisting of SOR1, SOR2, SOR3, and SOR4.

9. The ciliate of claim 8, wherein the polynucleotide molecule complementary to all or part of an RNA gene product is an antisense RNA or a double stranded RNA (dsRNA).

10. The ciliate of claim 1, wherein the ciliate is *Tetrahymena*.

11. A recombinant *Tetrahymena* germline genome comprising a genomic insertion or deletion in both copies of one or more SOR genes selected from the group consisting of SOR1, SOR2, SOR3, and SOR4.

12. The recombinant genome of claim 11, wherein the genomic insertion or deletion is located in the open reading frame of the one or more SOR genes.

13. The recombinant genome of claim 11 comprising a genomic insertion or deletion in both copies of 2, 3, or 4 SOR genes selected from the group consisting of SOR1, SOR2, SOR3, and SOR4.

14. A method of producing a genetically altered ciliate comprising:
   (a) transforming a ciliate with a polynucleotide comprising a sequence complementary to a SOR gene selected from the group consisting of SOR1, SOR2, SOR3, and SOR4; and
   (b) isolating a genetically altered ciliate wherein the ciliate lacks detectable expression of the gene product of said SOR gene.

15. The method of claim 14, wherein step (b) comprises isolating a genetically altered ciliate comprising an insertion or deletion in a SOR gene.

16. A method of producing a polypeptide comprising: expressing a polynucleotide encoding a polypeptide in the ciliate of claim 1.

17. The method of claim 16, further comprising:
   (c) purifying the expressed polypeptide from media.

18. The method of claim 16, wherein the polypeptide is not secreted by the ciliate.

19. The method of claim 18, further comprising:
   (c) purifying the ciliate from media.

20. The method of claim 19, further comprising:
   (d) purifying the polypeptide from the ciliate.

* * * * *